(12) United States Patent
Yang et al.

(10) Patent No.: US 10,876,892 B2
(45) Date of Patent: Dec. 29, 2020

(54) MEASURING BIOLOGICAL ANALYTES USING TIME-RESOLVED SPECTROSCOPY

(71) Applicant: BioSpex Inc., San Jose, CA (US)

(72) Inventors: William Yang, Los Altos Hills, CA (US); Leyun Zhu, Andover, MA (US); Chase Wang, Livermore, CA (US); Ming Chai, Union City, CA (US)

(73) Assignee: BioSpex, Inc., San Jose, CA (US)

( * ) Notice: Subject to any disclaimer, the term of this patent is extended or adjusted under 35 U.S.C. 154(b) by 378 days.

(21) Appl. No.: 15/847,876

(22) Filed: Dec. 19, 2017

(65) Prior Publication Data

US 2018/0313692 A1    Nov. 1, 2018

Related U.S. Application Data

(63) Continuation-in-part of application No. 15/582,428, filed on Apr. 28, 2017, now Pat. No. 10,548,481.

(51) Int. Cl.
*G01J 3/28* (2006.01)
*G01N 21/65* (2006.01)
(Continued)

(52) U.S. Cl.
CPC ............. *G01J 3/2889* (2013.01); *G01J 3/027* (2013.01); *G01J 3/10* (2013.01); *G01J 3/2803* (2013.01);
(Continued)

(58) Field of Classification Search
CPC .. G01J 3/2889; G01J 3/027; G01J 3/10; G01J 3/2803; G01J 3/44; G01J 2003/4424; G01N 21/65; G01N 21/39
See application file for complete search history.

(56) References Cited

U.S. PATENT DOCUMENTS 5,615,673 A    4/1997  Berger et al.
6,665,556 B1 * 12/2003  Alfano ................. A61B 5/0071
                                                          600/473
(Continued)

OTHER PUBLICATIONS

Cooper, John B. et al., "Sequentially Shifted Excitation Raman Spectroscopy: Novel Algorithm and Instrumentation for Fluorescence-Free Raman Spectroscopy in Spectral Space", Society for Applied Spectroscopy, vol. 67, No. 8, 2013, pp. 973-984.
(Continued)

*Primary Examiner* — Eric F Winakur
*Assistant Examiner* — Abid A Mustansir
(74) *Attorney, Agent, or Firm* — Carr & Ferrell LLP

(57) ABSTRACT

Systems and methods for time-resolved spectroscopy. Exemplary methods include: providing first, second, and third light using an excitation source; receiving first scattered light from a material responsive to the providing the first light; signaling the detector, after a delay, to provide a first spectrum of the received first scattered light; receiving second scattered light from the material responsive to the providing the second light; signaling the detector, after the delay, to provide a second spectrum of the received second scattered light; receiving third scattered light from the material responsive to the providing the third light; signaling the detector, after the delay, to provide a third spectrum of the received third scattered light; recovering a spectrum of the material using the first spectrum, second spectrum, and third spectrum; and identifying at least one molecule of the material using the recovered spectrum and a database of identified spectra.

20 Claims, 15 Drawing Sheets

(51) Int. Cl.
  *G01J 3/44* (2006.01)
  *G01J 3/10* (2006.01)
  *G01J 3/02* (2006.01)
  *G01N 21/39* (2006.01)

(52) U.S. Cl.
  CPC ............... *G01J 3/44* (2013.01); *G01N 21/65* (2013.01); *G01J 2003/4424* (2013.01); *G01N 21/39* (2013.01)

(56) References Cited

U.S. PATENT DOCUMENTS

| | | | |
|---|---|---|---|
| 7,647,092 | B2 | 1/2010 | Motz et al. |
| 8,072,595 | B1 * | 12/2011 | Bastiaans ................. G01J 3/44 356/301 |
| 8,325,337 | B2 | 12/2012 | Sinfield et al. |
| 8,570,507 | B1 | 10/2013 | Cooper et al. |
| 8,873,041 | B1 | 10/2014 | Chai et al. |
| 10,548,481 | B2 | 2/2020 | Yang et al. |
| 10,760,969 | B1 | 9/2020 | Wang et al. |
| 2003/0059820 | A1 * | 3/2003 | Vo-Dinh ............. B01J 19/0046 506/3 |
| 2007/0252978 | A1 | 11/2007 | Van Der Voort et al. |
| 2008/0129992 | A1 * | 6/2008 | Matousek ........... A61B 5/0059 356/301 |
| 2009/0105605 | A1 | 4/2009 | Abreu |
| 2011/0122407 | A1 * | 5/2011 | Jalali ..................... G01N 21/65 356/301 |
| 2012/0035442 | A1 | 2/2012 | Barman et al. |
| 2012/0287428 | A1 * | 11/2012 | Tamada ................... G01J 3/10 356/301 |
| 2013/0018237 | A1 | 1/2013 | Henneberg et al. |
| 2015/0233836 | A1 | 8/2015 | Okumura et al. |
| 2015/0342508 | A1 | 12/2015 | Chong |
| 2016/0354015 | A1 | 12/2016 | Zhang et al. |
| 2018/0164218 | A1 | 6/2018 | Zavaleta et al. |
| 2018/0310827 | A1 | 11/2018 | Yang et al. |
| 2019/0015023 | A1 | 1/2019 | Monfre |
| 2020/0124535 | A1 | 4/2020 | Yang et al. |
| 2020/0278255 | A1 | 9/2020 | Wang et al. |

OTHER PUBLICATIONS

Kostamovaara, J. et al., "Fluorescence suppression in Raman spectroscopy using a time-gated CMOS SPAD," Optics Express, Optics Society of America, vol. 21, No. 25, Dec. 13, 2013, 14 pages.

Nissinen, I. et al., "On the effects of the time gate position and width on the signal-to-noise ratio for detection of Raman spectrum in a time-gated CMOS single-photon avalanche diode based sensor," El Sevier, Sensors and Actuators B: Chemical, vol. 241, Mar. 31, 2017, pp. 1145-1152.

Kabuss, Julia et al., "Theory of time-resolved Raman scattering and fluorescence emission from semiconductor quantum dots",The American Physical Society, Physical Review B 81, 075314 (2010), Feb. 18, 2010.

* cited by examiner

900

| MOLECULE | DIAGNOSTIC FOR |
|---|---|
| Carotenoid | Antioxidant levels |
| Glucose (HbA1c test) | Diabetes |
| Colon cancer biomarker (BM) | Cancer |
| Liver cancer BM | Cancer |
| Lung cancer BM | Cancer |
| Melanoma BM | Cancer |
| Stomach cancer BM | Cancer |
| HDL Cholestrol | Heart disease |
| LDL Cholestrol | Heart disease |
| Triglycerides | Heart disease |

FIG. 9

MEASURING BIOLOGICAL ANALYTES USING TIME-RESOLVED SPECTROSCOPY

CROSS REFERENCE TO RELATED APPLICATION

This application is a continuation-in-part of application Ser. No. 15/582,428, filed Apr. 28, 2017.

TECHNICAL FIELD

The present technology relates generally to spectral imaging, and more specifically to time-resolved spectroscopy.

BACKGROUND

The approaches described in this section could be pursued but are not necessarily approaches that have previously been conceived or pursued. Therefore, unless otherwise indicated, it should not be assumed that any of the approaches described in this section qualify as prior art merely by virtue of their inclusion in this section.

Spectroscopy (or spectrography) refers to techniques that employ radiation in order to obtain data on the structure and properties of matter. Spectroscopy involves measuring and interpreting spectra that arise from the interaction of electromagnetic radiation (e.g., a form of energy propagated in the form of electromagnetic waves) with matter. Spectroscopy is concerned with the absorption, emission, or scattering of electromagnetic radiation by atoms or molecules.

Spectroscopy can include shining a beam of electromagnetic radiation onto a desired sample in order to observe how it responds to such stimulus. The response can be recorded as a function of radiation wavelength, and a plot of such responses can represent a spectrum. The energy of light (e.g., from low-energy radio waves to high-energy gamma-rays) can result in producing a spectrum.

SUMMARY

This summary is provided to introduce a selection of concepts in a simplified form that are further described in the Detailed Description below. This summary is not intended to identify key features or essential features of the claimed subject matter, nor is it intended to be used as an aid in determining the scope of the claimed subject matter.

The present disclosure is related to various systems and methods for time-resolved spectroscopy. Specifically, a method for time-resolved spectroscopy may comprise: providing first light using an excitation source; receiving first scattered light from a material responsive to the providing the first light using a detector; signaling the detector, after a delay commencing after the providing the first light, to provide a first spectrum of the received first scattered light, the delay being a predetermined amount of time beginning when the excitation source emits light; providing second light using the excitation source; receiving second scattered light from the material responsive to the providing the second light using the detector; signaling the detector, after the delay commencing after the providing the second light, to provide a second spectrum of the received second scattered light; providing third light using the excitation source; receiving third scattered light from the material responsive to the providing the third light using the detector; signaling the detector, after the delay commencing after the providing the third light, to provide a third spectrum of the received third scattered light; recovering a spectrum of the material using the first spectrum, second spectrum, and third spectrum; and identifying at least one molecule of the material using the recovered spectrum and a database of identified spectra.

BRIEF DESCRIPTION OF THE DRAWINGS

Embodiments are illustrated by way of example, and not by limitation, in the figures of the accompanying drawings, in which like references indicate similar elements and in which:

FIG. 9 is a table of molecules, according to some embodiments.

DETAILED DESCRIPTION

Figure 1:
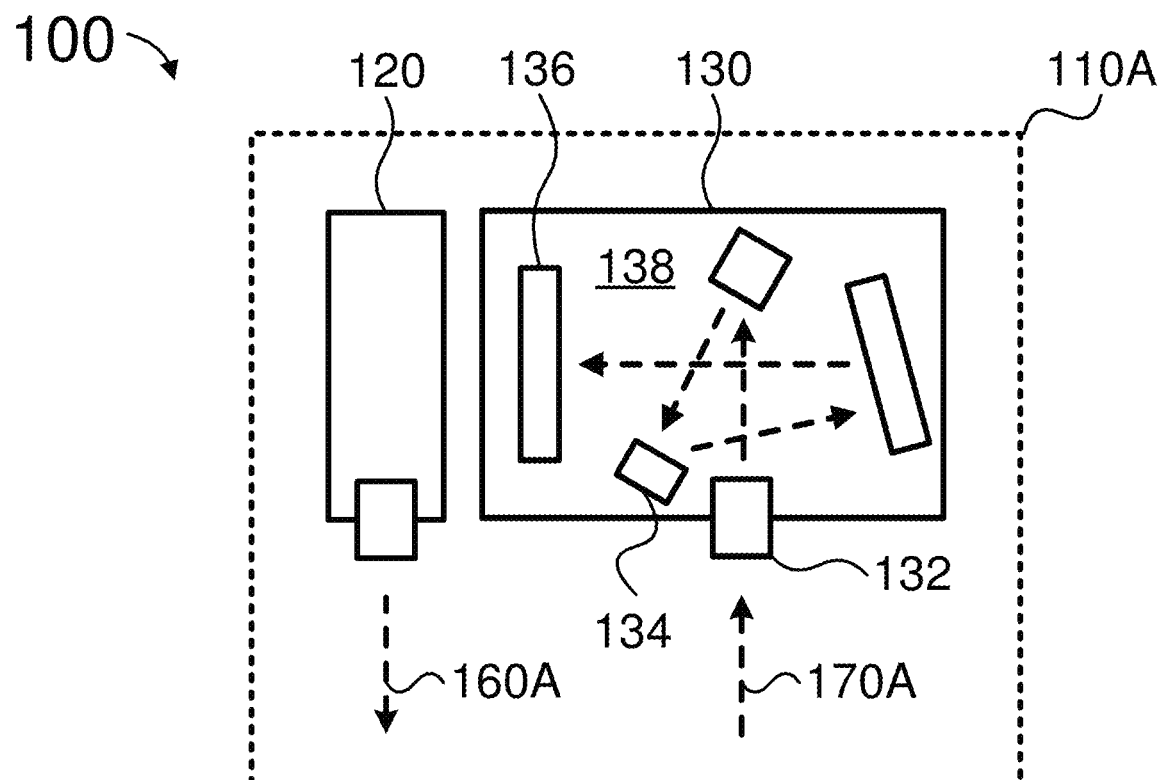
FIG. 1 is a simplified representation of a system for non-invasive measurement of biological analytes, according to some embodiments.
Figure 1:
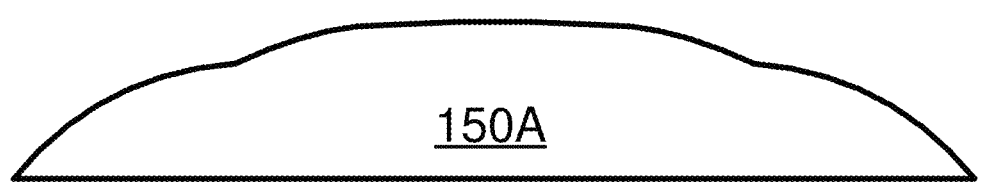

While this technology is susceptible of embodiment in many different forms, there is shown in the drawings and will herein be described in detail several specific embodiments with the understanding that the present disclosure is to be considered as an exemplification of the principles of the technology and is not intended to limit the technology to the embodiments illustrated. The terminology used herein is for the purpose of describing particular embodiments only and is not intended to be limiting of the technology. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof. It will be understood that like or analogous elements and/or components, referred to herein, may be identified throughout the drawings with like reference characters. It will be further understood that several of the figures are merely schematic representations of the present technology. As such, some of the components may have been distorted from their actual scale for pictorial clarity.

FIG. 1 illustrates system 100 for non-invasive measurement of biological analytes according to some embodiments. System 100 can include Raman instrument 110A and analyte 150A.

According to some embodiments, analyte 150A is at least one of plant, human, and animal tissue. For example, animal tissue is one or more of epithelial, nerve, connective, muscle, and vascular tissues. By way of further non-limiting example, plant tissue is one or more of meristematic (e.g., apical meristem and cambium), protective (e.g., epidermis and cork), fundamental (e.g., parenchyma, collenchyma and sclerenchyma), and vascular (e.g., xylem and phloem) tissues.

According to some embodiments, Raman instrument 110A comprises excitation light source 120, detector 130, and optional sampling apparatus 140. Excitation light source 120 is a monochromatic light source, such as a laser, in accordance with some embodiments. For example, excitation light source 120 is at least one of an Nd:YAG (neodymium-doped yttrium aluminium garnet; Nd:Y3Al5O12), Argon-ion, He—Ne, and diode laser. By way of further non-limiting example, excitation light source 120 can provide light (electromagnetic waves) in a range between ultraviolet (UV) light (e.g., electromagnetic radiation with a wavelength from 10 nm to 400 nm) and shortwave near-infrared (NIR) (1.4 μm to 3 μm), including portions of the electromagnetic spectrum in-between, such as visible light (e.g., 380 nm-760 nm) and NIR light (e.g., 0.75 μm to 1.4 μm).

In various embodiments, excitation light source 120 is tunable—a wavelength of the light from excitation light source 120 is changed by one or more (predetermined) increments and/or to one or more (predetermined) values— such as by using heat control (e.g., from a heating element), electrical control (e.g., using microelectromechanical systems (MEMS)), and mechanical control (e.g., using a mechanism to turn a mirror). Preferably, excitation light source 120 provides high spectral purity, high wavelength stability, and/or high power stability output.

Optional sampling apparatus 140 performs various combinations and permutations of directing light 160A from excitation light source 120, collecting the resulting Raman scatter (among others) 170A, filtering out radiation at the wavelength corresponding to the laser line (e.g., Rayleigh scattering), and providing the Raman scatter (among others) 170A to detector 130, according to some embodiments. For example, optional sampling apparatus 140 includes a microscope and/or an optical probe. By way of further non-limiting example, optional sampling apparatus 140 includes one or more filters (e.g., notch filter, edge-pass filter, and band-pass filter). Raman scatter (among others) 170A includes, for example, at least one of Raman scatter, fluorescence, and Rayleigh scattering (which can be filtered out by optional sampling apparatus 140).

In accordance with some embodiments, detector 130 is a spectrograph. For example, detector 130 includes slit 132, spectral dispersion element 134, and detector 136. By way of non-limiting example, detector 130 measures wavelengths in one or more of the UV spectrum (10 nm to 400 nm), visible spectrum (e.g., 380 nm-760 nm), visible to near-infrared (e.g., 400 nm-1000 nm), short-wave infrared (e.g., 950 nm-1700 nm), and infrared (e.g., 1 μm-5 μm).

Slit 132 can determine the amount of light (e.g., photon flux, such as Raman scatter (among others) 170A) that enters optical bench 138. Dimensions (e.g., height and width, not shown in FIG. 1) of slit 132 can determine the spectral resolution of detector 130. By way of non-limiting example, a height of slit 132 can range from 1 mm to 20 mm. By way of further non-limiting example, a width of slit 132 can range from 5 μm to 800 μm.

Spectral dispersion element 134 can determine a wavelength range of detector 130 and can partially determine an optical resolution of detector 130. For example, spectral dispersion element 134 is a ruled diffraction grating or a holographic diffraction grating, in the form of a reflective or transmission package. Spectral dispersion element 134 can include a groove frequency and a blaze angle.

Detector 136 receives light and measures the intensity of scattered light. Detector 136 can be a one- or two-dimensional detector array comprised of a semiconductor material such as silicon (Si) and indium gallium arsenide (InGaAs). In some embodiments, a bandgap energy of the semiconductor determines an upper wavelength limit of detector 136. An array of detector 136 can be in different configurations, such as charged coupled devices (CCDs), back-thinned charge coupled devices (BT-CCDs), complementary metal-oxide-semiconductor (CMOS) devices, and photodiode arrays (PDAs). CCDs can be one or more of intensified CCDs (ICCDs) with photocathodes, back illuminated CCDs, and CCDs with light enhancing coatings (e.g., Lumogen® from BASF®). Detector 136 has a resolution of 8-15 wavenumbers, according to some embodiments. Detector 136 can be used to detect concentrations of molecules in the range of 1-1,000 mg per deciliter (mg/dL).

Optical bench 138 of detector 130 includes slit 132, spectral dispersion element 134, detector 136, and various optical elements (not shown in FIG. 1). Slit 132, spectral dispersion element 134, and detector 136 can be arranged in optical bench 138, along with other components (e.g., monochromater—which transmits a mechanically selectable narrow band of wavelengths of light or other radiation chosen from a wider range of wavelengths available at an input— including one or more of a mirror, prism, collimater, holographic grating, diffraction grating, blazed grating, and the like), according to different configurations. For example, different configurations include: crossed Czerny-Turner, unfolded Czerny-Turner, transmission, and concave holographic optical benches.

Raman instrument 110A can provide information about molecular vibrations to identify and quantify characteristics (e.g., molecules) of analyte 150A. Raman instrument 110A can direct light 160A (electromagnetic waves) from excitation light source 120 (optionally through optional sampling apparatus 140) onto analyte 150A. Light 160A from excitation light source 120 can be said to be shone on analyte 150A and/or analyte 150A can be said to be illuminated by excitation light source 120 and/or light 160A. When (incident) light from excitation light source 120 hits analyte 150A, the (incident) light scatters. A majority (e.g., 99.999999%) of the scattered light is the same frequency as the light from excitation light source 120 (e.g., Rayleigh or elastic scattering).

A small amount of the scattered light (e.g., on the order of $10^{-6}$ to $10^{-8}$ of the intensity of the (incident) light from excitation light source 120) is shifted in energy from the frequency of light 160A from excitation light source 120.

The shift is due to interactions between (incident) light 160A from excitation light source 120 and the vibrational energy levels of molecules in analyte 150A. (Incident) Light 160A interacts with molecular vibrations, phonons, or other excitations in analyte 150A, causing the energy of the photons (of light 160A from excitation light source 120) to shift up or down (e.g., Raman or inelastic scattering). The shift in energy (e.g., of Raman scatter (among others) 170A from analyte 150A) can be used to identify and quantify characteristics (e.g., molecules) of analyte 150A.

Detector 130 detects (an intensity of) the Raman scattering using detector 136 (optionally received through optional sampling apparatus 140). A Raman spectrograph—a plot/graph of an intensity of the Raman scattering (shifted light) against frequency—can be produced by a computing system (not shown in FIG. 1) using intensity measurements from detector 130. The computing system can be integrated in or external to Raman instrument 110A. The Raman spectrograph can reliably be used to identify molecules in analyte 150A. In this way, a Raman spectrograph can be said to produce a "fingerprint" of molecules in analyte 150A. For example, a Raman spectrograph of analyte 150A can be compared to a database (e.g., in the same or another computing system) of Raman spectrographs associated with known molecules to identify and quantify molecules in analyte 150A.

According to some embodiments, Raman instrument 110A offers at least some of the advantages of: differentiating chemical structures (even if they contain the same atoms in different arrangements), physical contact with analyte 150A not required, no damage to analyte 150A (e.g., non-destructive testing), preparation of analyte 150A is not required, analyte 150A can be in a transparent container (e.g., when light 160A is in the visible or near-visible light spectrum), sensitivity to small changes in material structure (e.g., detection of molecular vibrations is very sensitive to changes in chemistry and structure), analyzing samples in aqueous solutions (e.g., suspensions, biological samples, etc.), and the like.

Figure 2:
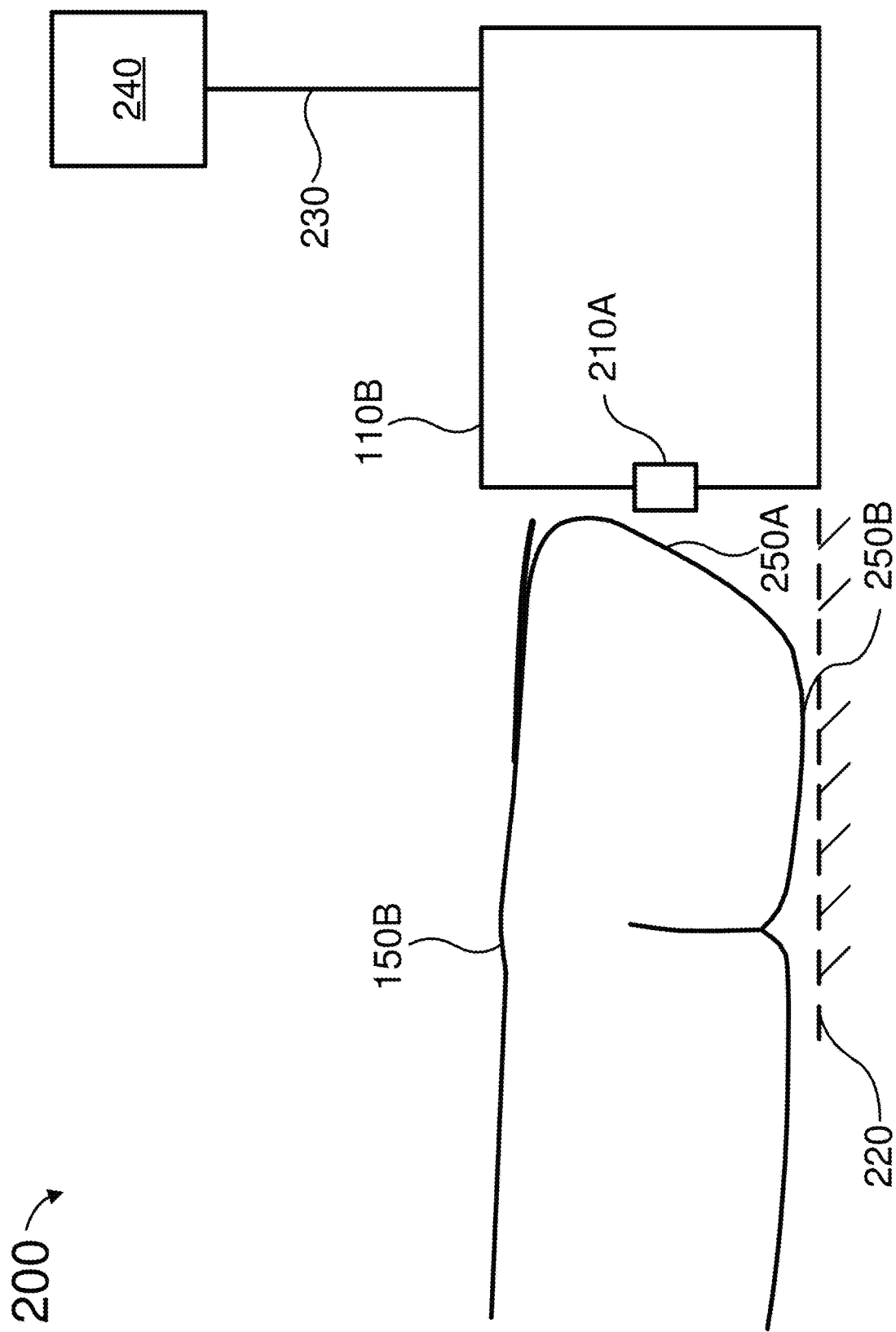
FIG. 2 is a simplified representation of a system for non-invasive measurement of biological analytes, according to various embodiments.

FIG. 2 illustrates system 200 for non-invasive measurement of biological analytes according to various embodiments. System 200 includes Raman instrument 110B and analyte 150B. Analyte 150B has at least some of the characteristics of analyte 150A (FIG. 1). Raman instrument 110E is depicted as being directed to a surface 250A of analyte 150B purely for illustrative purposes. Raman instrument 110E can be oriented toward other surfaces of analyte 150B, such as surface 250B. Moreover, analyte 150B is depicted as a (human) finger purely for illustrative purposes. Other plant or animal tissue can be used. Alternatively or additionally, other parts of a human body (e.g., including a blood vessel, such as an earlobe, neck, face, back, chest, arm, leg, toe, and the like) may be used.

Raman instrument 110E has at least some of the characteristics of Raman instrument 110A (FIG. 1). Raman instrument 110E can include aperture 210A. Aperture 210A can be an opening through which light 160A from excitation light source 120 (FIG. 1) exits Raman instrument 110E and/or through which Raman scatter (among others) 170A enters Raman instrument 110B. For example, analyte 150B is illuminated by excitation light source 120 through aperture 210A and the Raman scatter (among others) 170A (FIG. 1) from analyte 150B is received by detector 130 (FIG. 1) through aperture 210A. Aperture 210A can include at least some of the features of optional sampling apparatus 140 (FIG. 1). Although aperture 210A is shown as one opening, aperture 210A can be more than one opening.

Raman instrument 110E can optionally include surface 220. In some embodiments, surface 220 is a surface on which analyte 150B is placed so that analyte 150B is positioned for measurement by Raman instrument 110E and/or analyte 150B does not substantially move during operation of Raman instrument 110E (e.g., substantial movement would cause a sample to change between measurements).

Raman instrument 110E can be a portable, handheld, or compact unit which can operate on battery power. Raman instrument 110B can be communicatively coupled to computing system 240 through communications 230. Communications 230 can be various combinations and permutations of wired and wireless communications (e.g., networks) described below in relation to FIG. 10. Computing system 240 can include a database of Raman spectrographs associated with known molecules and/or remotely access the database over a communications network (not shown in FIG. 2). In some embodiments, computing system receives intensity measurements from Raman instrument 110B, produces at least one Raman spectrograph using data (e.g., intensity measurements) from Raman instrument 110B, and identifies and/or quantifies molecules in analyte 150B using the at least one Raman spectrograph and a database of Raman spectrographs associated with known molecules. Computing system 240 is described further below in relation to FIG. 10.

In some embodiments, computing system 240 is a single computing device. For example, computing system 240 is a desktop or notebook computer communicatively coupled to Raman instrument 110E through a Universal Serial Bus (USB) connection, a WiFi connection, and the like.

In various embodiments, computing system 240 is more than one (physical) computing device. For example, computing system 240 is a smartphone and a cloud-based computing system. The smartphone can receive data (e.g., intensity measurements) from Raman instrument 110B using USB, WiFi, Blutooth, and the like. The smartphone can optionally produce at least one Raman spectrum (e.g., including the Raman signal and fluorescence, for each excitation wavelength) using the data. The smartphone can transmit the data and/or at least one Raman spectrum to a cloud-based computing system over the Internet using a wireless network (e.g., cellular network). The cloud-based computing system can produce at least one Raman spectrum using the data, recover a Raman spectrograph (e.g., without fluorescence) from the at least one received/produced Raman spectrum, and/or quantify and/or identify molecules in analyte 150B using the recovered Raman spectrograph.

By way of further non-limiting example, communications 230 and at least some of computing system 240 can be in a dock (or cradle or pad) (not depicted in FIG. 2) in (or on or adjacent to) which Raman instrument 110E is placed. When Raman instrument 110E is placed in (or on or adjacent to) the dock, communications 230 between Raman instrument 110E and computing system 240 can be various combinations and permutations of wired and/or wireless communications. Alternatively or additionally, the dock can charge a rechargeable battery (e.g., lithium ion battery) of Raman instrument 110E using wired and/or wireless charging. For example, the dock can include a connector (or plug or socket or other electrical contacts) which mates with a connector (or socket or plug or other electrical contacts) of Raman instrument 110E (not depicted in FIG. 2) for communications and/or charging. By way of further non-limiting example, the dock (and Raman instrument 110B) can include at least one antenna, coil, and the like for wireless communications and/or charging. Other combinations and permutations of communications 230 and computing system 240 (e.g., as described below in relation to FIG. 10) may be used.

Figure 3:
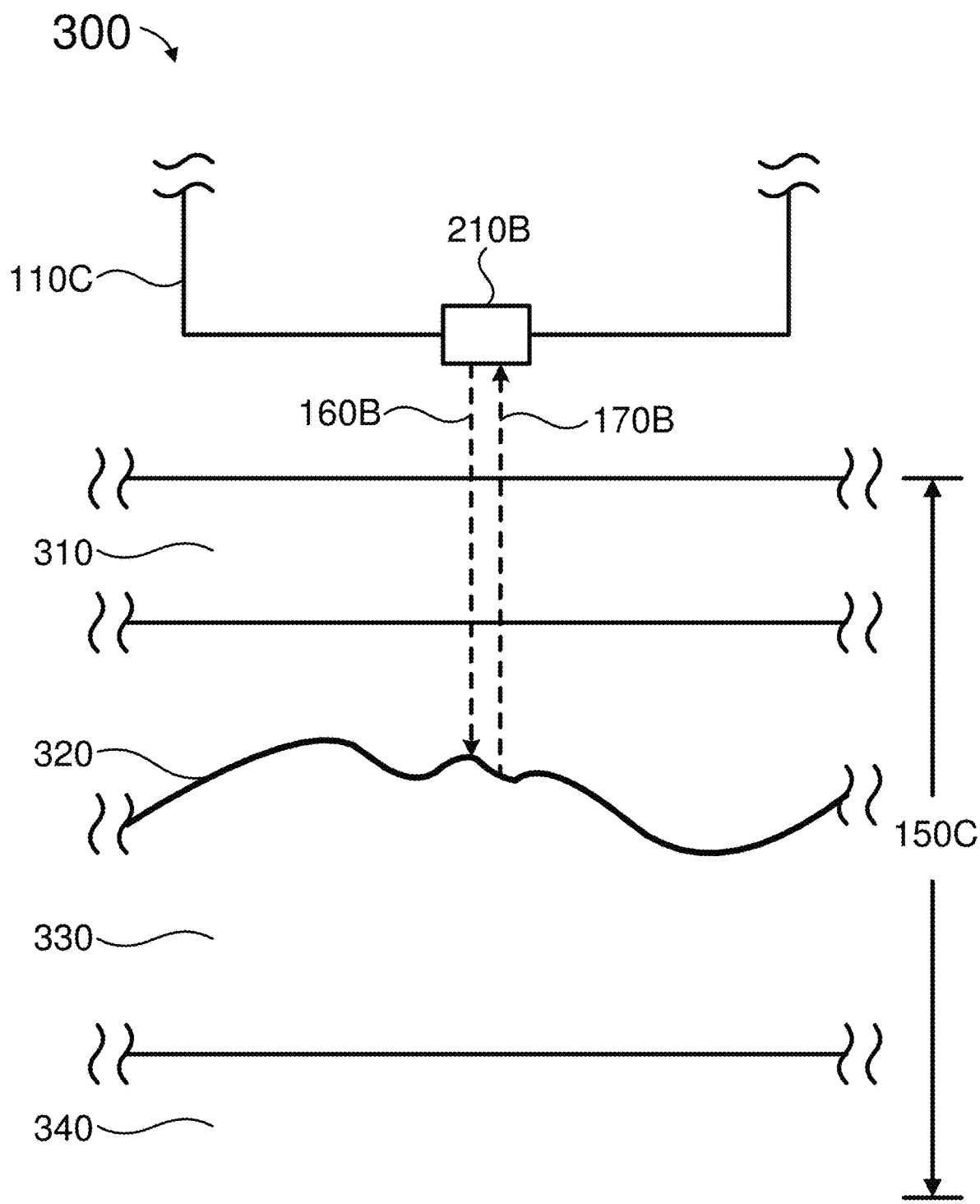
FIG. 3 is a cross-sectional view of the system of FIG. 2, in accordance with some embodiments.

FIG. 3 shows system 300, which is a simplified cross-sectional view of system 200 (FIG. 2) for non-invasive measurement of biological analytes, in accordance with some embodiments. System 300 includes Raman instrument 110C and analyte 150C. Raman instrument 110C has at least some of the characteristics of Raman instrument 110A (FIG. 1) and Raman instrument 110E (FIG. 2). Raman instrument 110C can include aperture 210B has at least some of the characteristics of aperture 210A (FIG. 2). Analyte 150C has at least some of the characteristics of analyte 150A (FIG. 1) and analyte 150B (FIG. 2).

Analyte 150C can include layers, such as epidermis 310, dermis 330, and subcutaneous (fatty) tissue 340. Dermis 330 includes blood vessel 320 (e.g., vein and/or artery). For pictorial clarity, some features of epidermis 310, dermis 330, and subcutaneous (fatty) tissue 340 (e.g., hair shaft, sweat pore and duct, sensory nerve ending, sebaceous gland, pressure sensor, hair follicle, stratum, and the like) are not shown in FIG. 3.

Light 160B can have at least some of the characteristics of light 160A (FIG. 1). Light 160B (e.g., from excitation light source 120 (FIG. 1)) illuminates analyte 150C through aperture 210B. Light 160B can pass through epidermis 310 to dermis 330. Photons of light 160B can bounce off molecules inside blood vessel 320. (Resulting) Raman scatter (among others) 170B is received by detector 130 (FIG. 1) through aperture 210B. Raman scatter (among others) 170B can have at least some of the characteristics of Raman scatter (among others) 170A (FIG. 1).

Figure 4A:
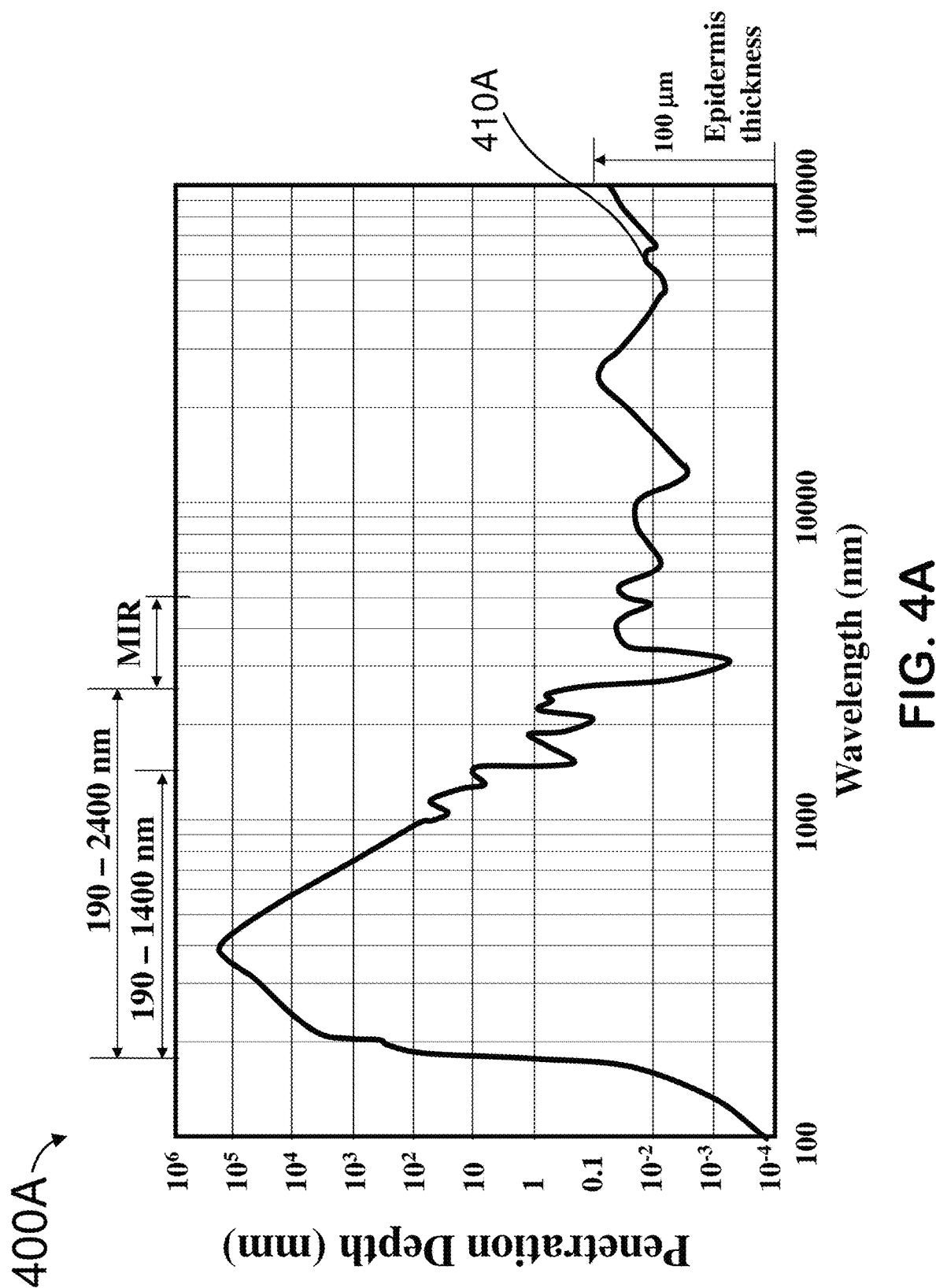
FIGS. 4A and 4B are graphical representations of penetration depth into liquid water and absorption spectra of biological tissues, respectively, in accordance with various embodiments.

FIG. 4A depicts graphical representation (e.g., plot, graph, and the like) 400A of penetration depth 410A into liquid water of light over excitation wavelength. By way of non-limiting example, an epidermis (e.g., epidermis 310 in FIG. 3) can have a thickness on the order of 100 μm, so an excitation wavelength of light (e.g., light 160A and light 160B in FIGS. 1 and 3, respectfully) can be advantageously selected such that a penetration depth is at least 100 μm (e.g., approximately 190 nm to 2400 nm). In some embodiments, the excitation wavelength of light is in a range of 670 nm-900 nm for (human) tissue. Other ranges for the excitation wavelength of light can be used (e.g., depending on the depth of the tissue to be studied).

Figure 4B:
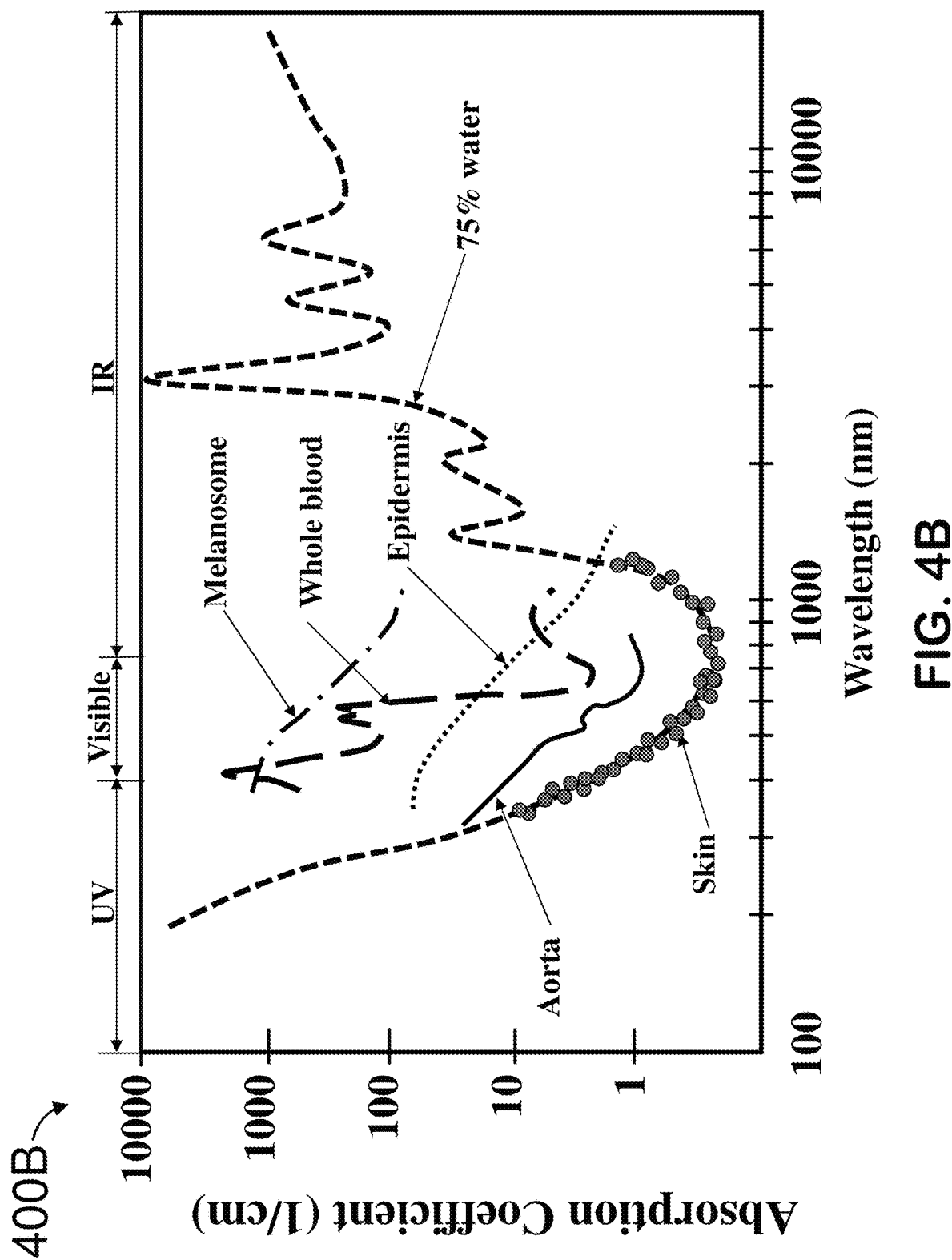

FIG. 4B shows graphical representation (e.g., plot, graph, and the like) 400B of absorption spectra of various tissues over excitation wavelength. By way of non-limiting example, an excitation wavelength of light (e.g., light 160A and light 160B in FIGS. 1 and 3, respectfully) can be advantageously selected to minimize the absorption coefficient so as to minimize absorption of the light by the tissue to be studied (e.g., so the light can scatter and be detected). When the tissue substantially absorbs light and/or Raman scatter (among others) (e.g., 170A and 170B in FIGS. 1 and 3, respectively), there can be insufficient electromagnetic radiation for detector 130 to detect. In various embodiments, the excitation wavelength of light is in a range of 670 nm-900 nm for (human) tissue. Other ranges for the excitation wavelength of light can be used (e.g., depending on the absorption coefficient of the tissue to be studied).

In embodiments where analyte (e.g., 150A-C (FIGS. 1-3)) is a live (and not dead) animal (e.g., living, alive, etc.), blood flows through blood vessel 320 (FIG. 3). Blood flow through blood vessel 320 in animals (e.g., humans) is caused by a heart (not shown in FIG. 4) pumping blood (e.g., beating heart). When measurements are taken at a rate slower than blood flows, different samples of blood are measured instead of the same sample and fluorescence will change with each sample.

When Raman instrument 110C takes multiple measurements (as described below in relation to FIGS. 6 and 7), the measurements can be taken before the molecules in blood illuminated in one measurement (e.g., blood sample) flow away and are not available for the next measurement. For example, a resting adult human heart can beat at approximately 60 to 100 beats a minute (~1 Hz). Raman instrument 110C can take measurements within a tenth of a second (~0.1 KHz) or less, such that measurements are taken faster than blood flows (e.g., multiple measurements are taken from the same (instead of different) sample). Slower and/or faster sampling rates (e.g., frequency at which measurements are taken) can be used depending on the heart rate associated with analyte 150C (FIG. 3). In various embodiments, the sampling rate is 10 Hz-1 KHz.

Figure 5:
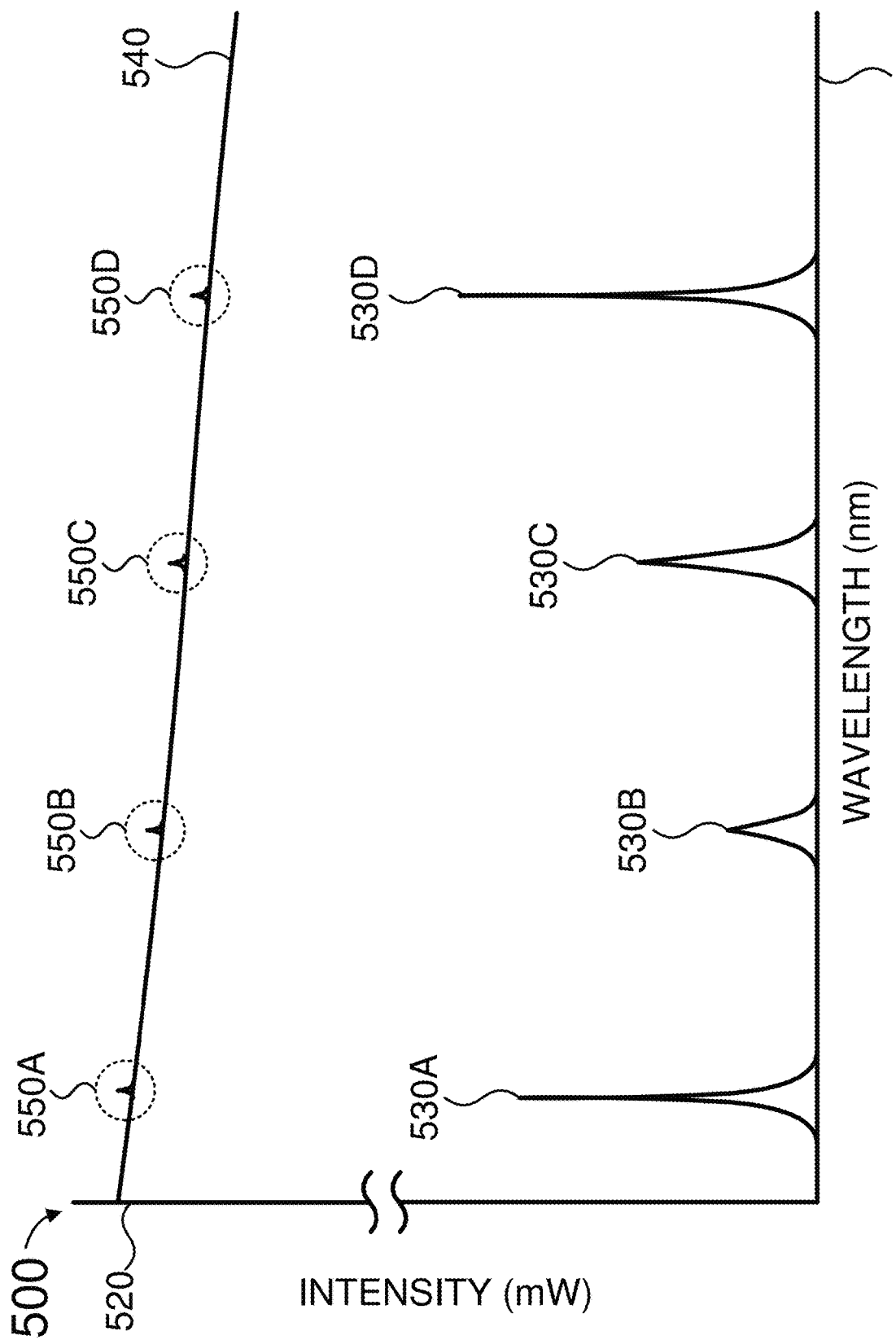
FIG. 5 is a simplified graphical representation of intensity, according to some embodiments.

FIG. 5 illustrates graphical representation (e.g., plot, graph, and the like) 500 of received light intensity (e.g., in milliwatts (mW)) along axis 520 over received light wavelength (e.g., in nanometers (nm)) along axis 510. Graphical representation 500 includes Raman signal 530 (530A-530D) and fluorescence 540, according to some embodiments. Raman signal 530 is a Raman spectrograph for an analyte (e.g., analyte 150A-C (FIGS. 1-3) that would be measured if it were not overwhelmed/obscured by fluorescence 540. Although Raman signal 530 is shown having four peaks at regular intervals, Raman signal 530 may have any number of peaks having different intensities and occurring at different/irregular frequencies. The peaks of Raman signal 530 can indicate information about different molecular bonds.

When light (e.g., light 160A and 160B in FIGS. 1 and 3, respectively) illuminates analyte (e.g., analyte 150A-C in FIGS. 1-3, respectively), fluorescence 540 (in addition to Raman signal 530 (530A-530D)) can result. Fluorescence 540 can be several orders of magnitude (e.g. $10^5$-$10^6$) higher in intensity than Raman signal 530. Fluorescence 540 can overwhelm or obscure Raman signal 530, such that Raman signal 530 is difficult to actually measure.

An intensity measured by detector 130 (FIG. 1) includes an intensity (I) of the Raman signal ($I_R$) and intensity of fluorescence ($I_F$) at each wavelength (e.g., $I=I_R+I_F$). For example, the intensity measured by detector 130 (FIG. 1) would look like fluorescence 540 with very small contributions 550A-550D from Raman signal 530 (530A-530D). Contributions 550A-550D are provided for illustrative purposes and are not drawn to scale. Fluorescence 540 is several orders of magnitude (e.g. $10^5$-$10^6$) larger than Raman signal 530 and contributions 550A-550D and may not be visible if shown to scale.

An intensity of the Raman signal is inversely proportional to the excitation wavelength (λ) of light (e.g., light 160A and 160B in FIGS. 1 and 3, respectively) (e.g., Raman signal strength $\alpha\lambda^{-4}$). In contrast, an intensity of the fluorescence is proportional to the excitation wavelength (λ). Generally, when a longer excitation wavelength (λ) is used to illuminate tissue, there is less fluorescence but the Raman signal strength becomes smaller and difficult to measure. Likewise, when a shorter excitation wavelength (λ) is used (e.g., in the near infrared (NR) spectrum) to illuminate tissue, too much fluorescence is produced making it difficult to measure the Raman signal.

Figure 6:
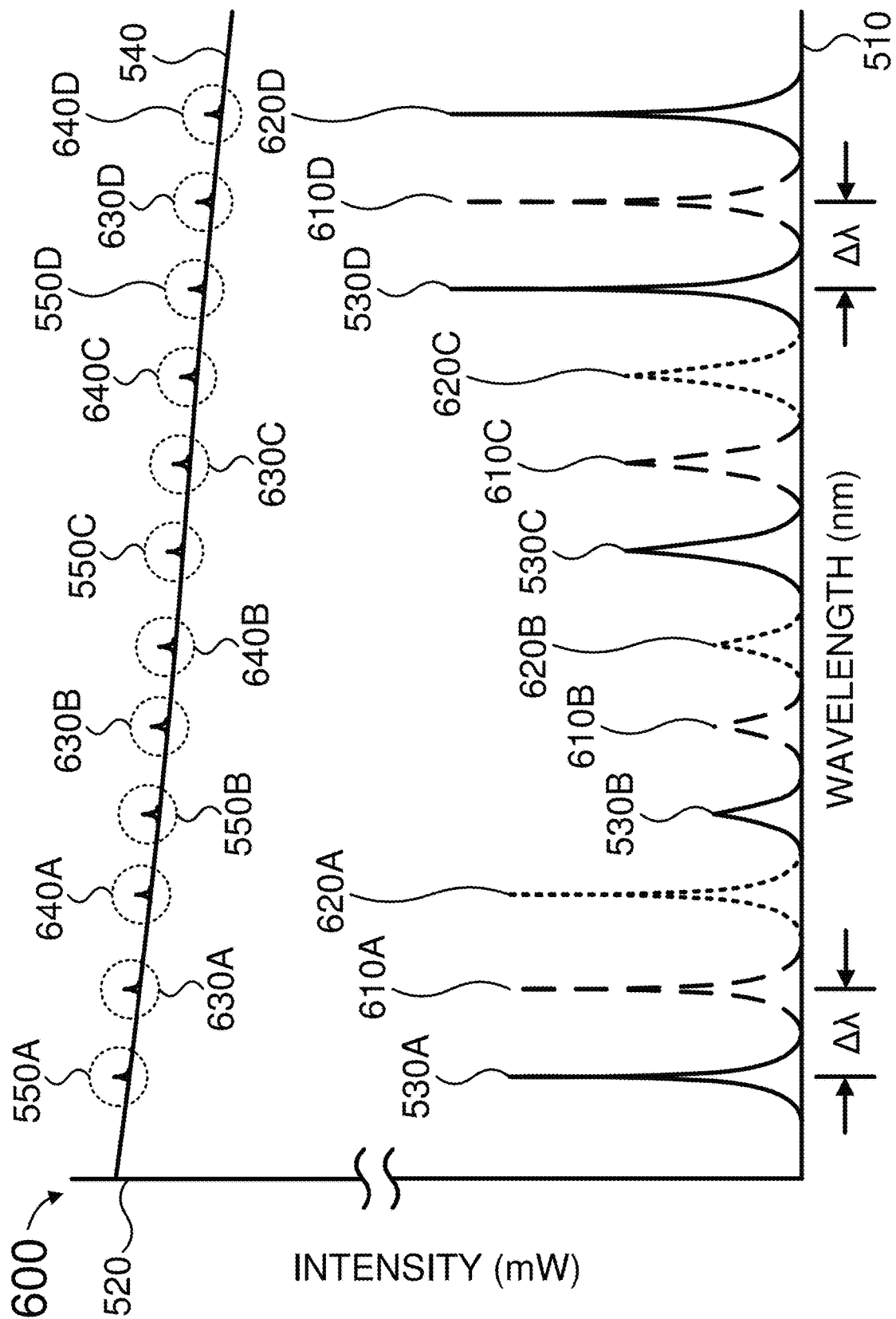
FIG. 6 is a simplified graphical representation of intensity for more than one excitation wavelength, according to various embodiments.

FIG. 6 depicts graphical representation (e.g., plot, graph, and the like) 600 of received light intensity (e.g., in milliwatts (mW)) along axis 520 over received light wavelength (e.g., in nanometers (nm)) along axis 510, according to some embodiments. Graphical representation 600 includes Raman signal 530 (530A-530D), Raman signal 610 (610A-610D), Raman signal 620 (620A-620D), and fluorescence 540. Raman signal 530 and fluorescence 540 were described above in relation to FIG. 5. Raman signals 610 and 620 are Raman spectrographs for analyte 150C (FIG. 3) that would be measured if it were not overwhelmed/obscured by fluorescence 540. Although Raman signals 610 and 620 are shown each having four peaks at regular intervals, Raman signals 610 and 620 may have any number of peaks having different intensities and occurring at different/irregular frequencies (e.g., corresponding to or following Raman signal 530). Raman signals 530, 610, and 620 can result from different excitation wavelengths (λ).

As described above, excitation light source 120 (FIG. 1) can be tunable, such that an excitation wavelength can change (e.g., by a predetermined increment, to one or more predetermined wavelengths, etc.). When measurements are (sequentially) taken at different excitation wavelengths (λ) (e.g., $\lambda = \lambda_0, \lambda_1, \lambda_2, \ldots$), a Raman signal for each excitation wavelength can be produced. For example, Raman signal 530 (530A-530D) is measured at $\lambda = \lambda_0$, Raman signal 610 (610A-610D) at $\lambda = \lambda_1$, and Raman signal 620 (620A-620D) $\lambda = \lambda_2$. Although three different excitation wavelengths (e.g., $\lambda = \lambda_0, \lambda_1, \lambda_2$) are used, any number N of different excitation wavelengths can be used (e.g., $\lambda = \lambda_0, \lambda_1, \ldots \lambda_N$). N can be a function of a sampling rate of Raman instrument (e.g., Raman instrument 110A (FIG. 1), 110B (FIG. 2), and 110C (FIG. 3)), a molecule to be detected and/or quantified, and the like. The excitation wavelength can be incremented by a predetermined amount $\Delta\lambda$, such that $\lambda_1 = \lambda_0 + \Delta\lambda$, $\lambda_2 = \lambda_1 + \Delta\lambda$, $\lambda_3 = \lambda_2 + \Delta\lambda$, etc. As shown in FIG. 6, Raman signals 610 and 620 can be shifted from an adjacent Raman signal (e.g., Raman signals 530 and 610, respectively) by $\Delta\lambda$. Although Raman signals 530, 610, and 620 are shifted (e.g., by $\Delta\lambda$), the envelopes (e.g., amplitude and frequency of the peaks) of Raman signals 530, 610, and 620 are consistent. At each of $\lambda = \lambda_0, \lambda_1, \lambda_2, \ldots$, fluorescence 540 is the same (e.g., as long as the (blood) sample does not change).

An intensity measured by detector 130 (FIG. 1) includes an intensity (I) of the Raman signal ($I_R$) and intensity of fluorescence ($I_F$) at each wavelength (e.g., $I = I_R + I_F$), as described above in relation to FIG. 5. For example, for excitation wavelength $\lambda = \lambda_1$, the Raman spectrograph would look like fluorescence 540 with very small contributions (e.g., contributions 630A-D) from Raman signal 610 (610A-610D). By way of further non-limiting example, for excitation wavelength $\lambda = \lambda_2$, the Raman spectrograph would look like fluorescence 540 with very small contributions (e.g., 640A-D) from Raman signal 620 (620A-620D). Contributions 630A-D and 640A-D are provided for illustrative purposes and are not drawn to scale.

As described below in relation to FIGS. 7 and 8, a Raman spectrograph for analyte 150C (e.g., compensating for fluorescence) can be produced using Raman signals 530 (530A-530D), 610 (610A-610D), 620 (620A-620D), etc.

Figure 7:
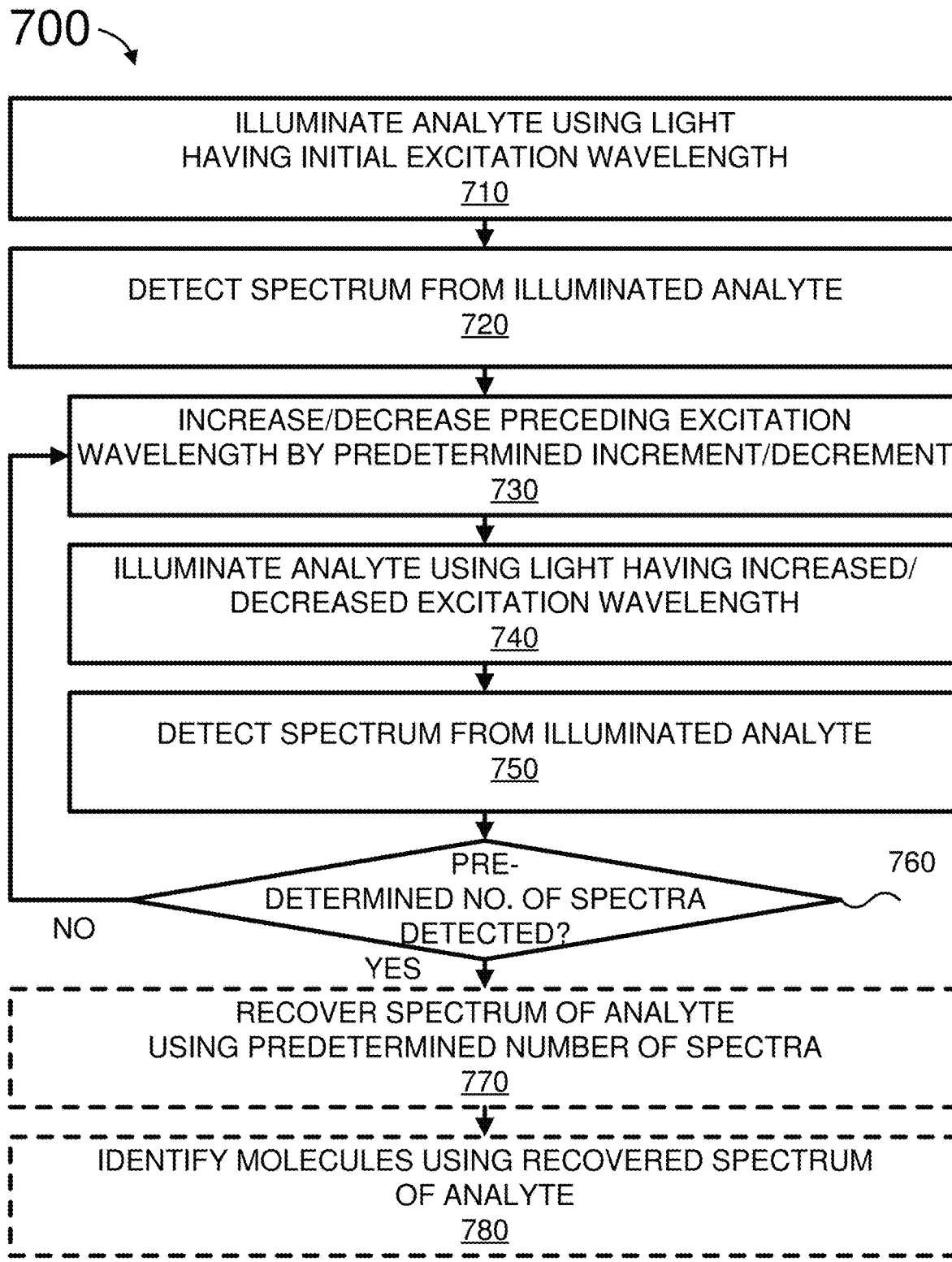
FIG. 7 is a simplified flow diagram of a method for non-invasive measurement of biological analytes, in accordance with some embodiments.
Figure 10:
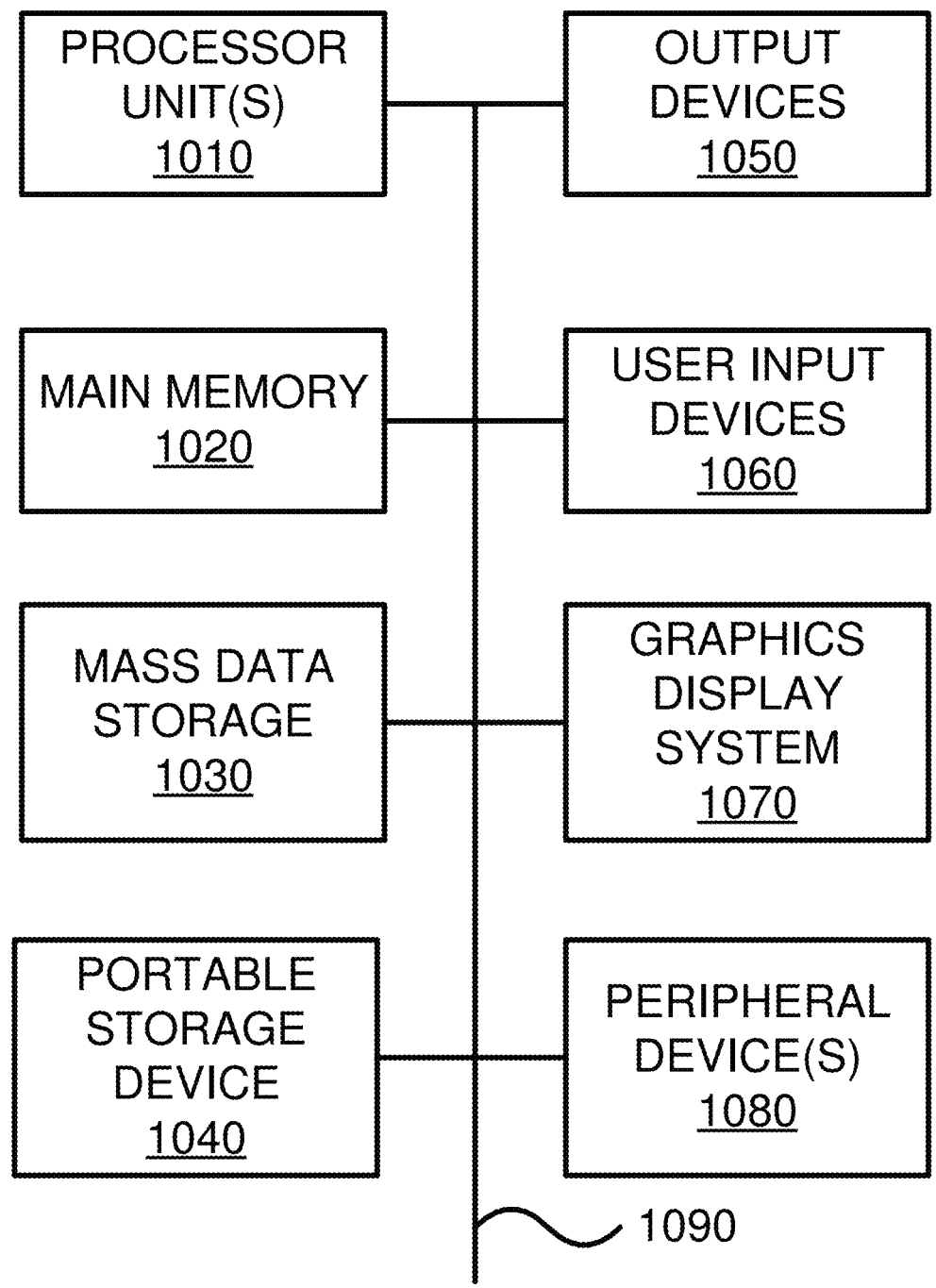
FIG. 10 is a simplified block diagram of a computing system, according to various embodiments.

FIG. 7 illustrates method 700 for non-invasive measurement of biological analytes, according to some embodiments. Method 700 can be performed by a Raman instrument and/or a computing system. The Raman instrument can have at least some of the characteristics of Raman instrument 110A (FIG. 1), Raman instrument 110B (FIG. 2), and Raman instrument 110C (FIG. 3). The computing system can have at least some of the characteristics of computing system 240 (FIG. 2) and computing system 1000 (FIG. 10).

Method 700 can commence at step 710, where an analyte can be illuminated using light having an initial excitation wavelength. For example, the analyte has at least some of the characteristics of analyte 150A (FIG. 1), analyte 150B (FIG. 2), and analyte 150C (FIG. 3). By way of further non-limiting example, the light can be provided by the Raman instrument, for example, using excitation light source 120 (FIG. 1). For illustrative purposes, the initial excitation wavelength can referred to as $\lambda_0$ and can have a value of 670 nm (e.g., $\lambda_0 = 670$ nm). Other values for $\lambda_0$ can be used.

At step 720, a spectrum (e.g., including Raman scattering (or Raman signal) and fluorescence) can be detected from the illuminated analyte. In some embodiments, the light hitting the analyte results in Raman scattering (or Raman signal) and fluorescence. For example, the Raman scattering (e.g., contributions 550A-D, 630A-D, and 640A-D) and fluorescence (e.g., fluorescence 540) can be detected by the Raman instrument (e.g., using detector 130 optionally through optional sampling apparatus 140 (FIG. 1)). By way of further non-limiting example, the detected Raman scattering (e.g., contributions 550A-D) and fluorescence (e.g., fluorescence 540) may appear (e.g., when graphed, plotted, and the like) as shown in graphical representation 500 (FIG. 5) (where the excitation wavelength is $\lambda_0$). The detected spectrum (e.g., data, graphical representation, and the like) can be stored in the Raman instrument and/or the computing system.

At step 730, the preceding excitation wavelength can be increased or decreased by a predetermined increment or decrement, respectively. For illustrative purposes, the predetermined increment/decrement can be referred to as $\Delta\lambda$. For example, when the preceding excitation wavelength is $\lambda_0$, an increased/decreased excitation wavelength is $\lambda_1$, where $\lambda_1 = \lambda_0 + \Delta\lambda$. By way of further non-limiting example, when the preceding excitation wavelength is $\lambda_1$, an increased/decreased excitation wavelength is $\lambda_2$, where $\lambda_2 = \lambda_1 + \Delta\lambda$. By way of additional non-limiting example, when N spectra are to be detected, $\lambda_A = \lambda_0 + (A \ast \Delta\lambda)$, where $A = \{0, 1, \ldots (N-1)\}$.

For illustrative purposes, the predetermined increment/decrement can have a value of 0.5 nm. To illustrate embodiments where the excitation wavelength is increased, when $\lambda_0 = 670$ nm, $\lambda_1 = 670.5$ nm, $\lambda_2 = 671$ nm, and so on according to the number of spectra to be detected (N). In some embodiments, the excitation wavelength is decreased by a decrement.

At step 740, the analyte can be illuminated using light having the increased or decreased wavelength. To illustrate embodiments where the excitation wavelength is increased, the light can have a wavelength $\lambda_1 = 670.5$ nm, $\lambda_2 = 671$ nm, or so on according to the number of spectra to be detected (N).

At step 750, a spectrum (e.g., including Raman scattering (or Raman signal) and fluorescence) can be detected from the illuminated analyte. In some embodiments, the light (having the increased/decreased excitation wavelength) hitting the analyte results in Raman scattering (or Raman signal) and fluorescence. For example, the Raman scattering and fluorescence can be detected by the Raman instrument (e.g., using detector 130 optionally through optional sampling apparatus 140 (FIG. 1)). The detected Raman scattering and fluorescence may appear (e.g., when graphed/plotted) as shown in graphical representation 500 (FIG. 5) (where the excitation wavelength is the the increased/decreased excitation wavelength, for example, $\lambda_1, \lambda_2$, and so on according to the number of spectra to be detected). Each detected spectrum (e.g., data, graphical representation, and the like) can be stored by (and/or in) the Raman instrument and/or the computing system.

At step 760, a determination is made as to whether another spectrum is to be detected. In some embodiments, the predetermined number of spectra to be detected (N) is compared to the number of spectra (actually) detected. When the predetermined number of spectra to be detected (N) is less than the number of spectra detected, method 700 can proceed to step 730. When the predetermined number of spectra to be detected (N) is equal to the number of spectra actually detected, method 700 can proceed to step 770. For example, when N=6 and spectra are already detected for $\lambda_0$, $\lambda_1$, $\lambda_2$, $\lambda_3$, $\lambda_4$, and $\lambda_5$, method 700 can proceed to step 770. By way of further non-limiting example, when N=3 the detected Raman scattering and fluorescence (e.g., detected for each of $\lambda_0$, $\lambda_1$, and $\lambda_2$) may appear (e.g., when graphed/plotted together) as shown in graphical representation 600 (FIG. 6).

Optionally at step 770, a Raman spectrum of the analyte can be recovered using the detected spectra (e.g., N detected spectra). In some embodiments, the Raman spectrum of the analyte can be recovered using expectation maximization techniques. The recovered Raman spectrum may appear (e.g., when graphed/plotted) as shown in graphical representation 500 (FIG. 5) (e.g., Raman signal 530 (530A-D) without fluorescence 540). Recovering the Raman spectrum of the analyte is described further below in relation to FIG. 8.

Optionally at step 780, a molecule can be identified using the recovered Raman spectrum. For example, a database of known Raman spectrum for certain molecules can be searched using (e.g., compared to) the recovered Raman spectrum to find a match.

Figure 8:
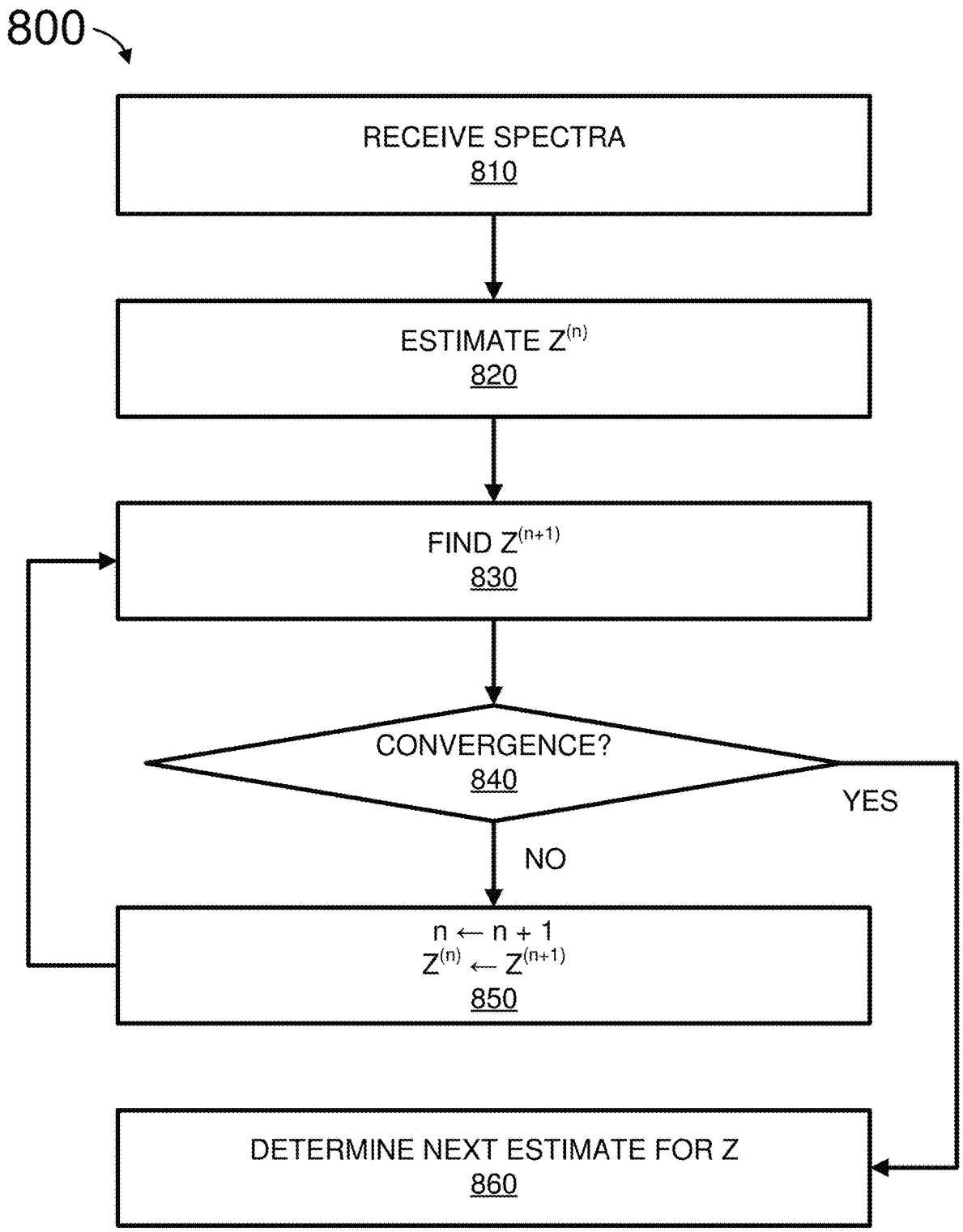
FIG. 8 is a simplified flow diagram of a method for recovering a Raman spectrum, in accordance with various embodiments.

FIG. 8 shows method 800 for recovering a Raman spectrum of an analyte using expectation maximization techniques and the detected spectra, according to some embodiments. Method 800 can commence at Step 810, where the detected spectra (e.g., N detected spectra) can be received. By way of non-limiting example, the detected spectra are referred to as vector X. The detected intensity in vector X includes the intensity of fluorescence and the Raman signal (e.g., $I=I_R+I_F$). According to some embodiments, vector X (e.g., detected spectra) can be represented by:

$$X = \begin{bmatrix} Y_{1,1} \\ Y_{1,2} \\ \vdots \\ Y_{1,N} \\ Y_{2,1} \\ Y_{2,2} \\ \vdots \\ Y_{2,N} \\ \vdots \\ Y_{K-1,N} \\ Y_{K,1} \\ Y_{K,2} \\ \vdots \\ Y_{K,N} \end{bmatrix} \quad (1)$$

where each $Y_i$ (where i={1, 2, ... K}) is a measured spectra using a different excitation wavelength.

By way of further non-limiting example, the (separate) values of the fluorescence and the Raman signal are referred to as vector Z. Vector Z (e.g., (separate) values of the fluorescence and the Raman signal) can be represented by a vector have 2N dimensions:

$$X = \begin{bmatrix} S_1^F \\ S_2^F \\ \vdots \\ S_N^F \\ S_1^R \\ S_2^R \\ \vdots \\ S_N^R \end{bmatrix} \quad (2)$$

where the fluorescence spectrum is $S^F$ and the Raman spectrum is $S^R$.

A relationship between vector X and vector Z can be represented as a matrix of (predetermined) parameters, matrix H. By way of non-limiting example, a relationship between vector X, vector Z, and matrix H can be:

$$H \times Z = X \quad (3)$$

where matrix H can be represented by a KN×2N matrix having predetermined values, such as:

$$H = \begin{bmatrix} 1, 0, 0, \ldots, 0 \\ 0, 1, 0, \ldots, 0 \\ \vdots \\ 0, 0, 0, \ldots, 1 \\ 0, 0, 0, \ldots, 0 \\ 1, 0, 0, \ldots, 0 \\ 0, 1, 0, \ldots, 0 \\ \vdots \\ 0, 0, 0, \ldots, 1 \end{bmatrix} \quad (4)$$

The relationship depicted in equation 3 is an inverse problem: using a known vector X to determine vector Z, where matrix H is a large matrix which cannot be inverted. In various embodiments, the inverse problem in equation 3 is solved using Maximum Likelihood-Expectation Maximization (ML-EM) iterative methods included in method 800. For example, among all possible values for vector Z, one that maximizes the probability of producing vector X is selected. The maximization can be performed using the Expectation Maximization (EM) techniques included in method 800.

At step 820, an initial guess vector $Z^{(n=0)}$ can be used for vector Z (e.g., $S^F$ and $S^R$). In some embodiments, vector $Z^{(n=0)}$ can be arbitrary, a prior calculated estimate of vector Z (e.g., using method 800), combinations thereof, and the like.

At step 830, an estimate for vector Z (e.g., $Z^{(n+1)}$) can be determined. For example, Z can be estimated using:

$$z_i^{(n+1)} = z_i^n * \left( \frac{1}{\sum_j H_{ji}} \right) * \left( \sum_j H_{ji} \right) * \left( \frac{x_j}{\sum_k H_{jk} z_k^n} \right) \quad (5)$$

At step 840, the estimate for vector Z (e.g., vector $Z^{(n+1)}$) can be evaluated. In some embodiments, the estimate for vector Z is evaluated for convergence. For example, when a change between successive iterations (e.g., between vector $Z^n$ and vector $Z^{n+k}$, where k can be a number in the range of 0-10,000) is smaller than a predetermined amount (e.g., tolerance, such as 1%-10% change), then vector Z can be said to converge. The change can be determined between an iteration early in the method (e.g., vector $Z^j$ (where j can be a number in the range of 5-10,000) and a latest iteration. Additionally or alternatively, vector Z can be said to have converged after a predetermined number (e.g., 10-50,000) of iterations. In various embodiments, for some spectra having different fluorescence levels, changes in the estimate for vector Z are negligible (e.g., smaller than a predetermined amount) after around 2,000 iterations (e.g., 1,000-3,000 iterations). When vector Z has not converged or immediately after the first iteration (e.g., using vector $Z^{(n=0)}$), method 800 can proceed to step 850. When vector Z is determined to have converged, method 800 can proceed to step 860.

At step 850, n can be incremented (e.g., n←n+1), Z can be incremented (e.g., $Z^{(n)}$←$Z^{(n+1)}$) and method 800 can perform another iteration by proceeding to step 830.

At step 860, a next estimate for vector Z can be determined using vector X, matrix H, and the estimate for vector Z calculated in the prior iteration.

In various embodiments, method 800 can be performed multiple times, each repetition using a different initial guess $Z^{(n=0)}$. For example, the initial guesses can be various combinations and permutations of arbitrary, prior calculated estimate of Z (e.g., using method 800), and the like. A vector Z can be selected from among the repetitions of method 800.

FIG. 9 depicts a table 900 of example molecules 910 which may be detected by the systems (e.g., system 100 (FIG. 1), system 200 (FIG. 2), and system 200 (FIG. 2)) and detected using methods (e.g., method 700 (FIG. 7) and method 800 (FIG. 8)) described herein. Conditions 920 associated with each molecule 910 are shown for illustrative purposes.

FIG. 10 illustrates an exemplary computer system (or computing system) 1000 that may be used to implement some embodiments of the present invention. The computer system 1000 in FIG. 10 may be implemented in the contexts of the likes of computing systems, networks, servers, or combinations thereof. The computer system 1000 in FIG. 10 includes processor unit(s) 1010 and main memory 1020. Main memory 1020 stores, in part, instructions and data for execution by processor unit(s) 1010. Main memory 1020 stores the executable code when in operation, in this example. The computer system 1000 in FIG. 10 further includes a mass data storage 1030, portable storage device 1040, output devices 1050, user input devices 1060, a graphics display system 1070, and peripheral device(s) 1080.

The components shown in FIG. 10 are depicted as being connected via a single bus 1090. The components may be connected through one or more data transport means. Processor unit(s) 1010 and main memory 1020 are connected via a local microprocessor bus, and the mass data storage 1030, peripheral device(s) 1080, portable storage device 1040, and graphics display system 1070 are connected via one or more input/output (I/O) buses.

Mass data storage 1030, which can be implemented with a magnetic disk drive, solid state drive, or an optical disk drive, is a non-volatile storage device for storing data and instructions for use by processor unit(s) 1010. Mass data storage 1030 stores the system software for implementing embodiments of the present disclosure for purposes of loading that software into main memory 1020.

Portable storage device 1040 operates in conjunction with a portable non-volatile storage medium, such as a flash drive, floppy disk, compact disk, digital video disc, or Universal Serial Bus (USB) storage device, to input and output data and code to and from the computer system 1000 in FIG. 10. The system software for implementing embodiments of the present disclosure is stored on such a portable medium and input to the computer system 1000 via the portable storage device 1040.

User input devices 1060 can provide a portion of a user interface. User input devices 1060 may include one or more microphones, an alphanumeric keypad, such as a keyboard, for inputting alphanumeric and other information, or a pointing device, such as a mouse, a trackball, stylus, or cursor direction keys. User input devices 1060 can also include a touchscreen. Additionally, the computer system 1000 as shown in FIG. 10 includes output devices 1050. Suitable output devices 1050 include speakers, printers, network interfaces, and monitors.

Graphics display system 1070 include a liquid crystal display (LCD) or other suitable display device. Graphics display system 1070 is configurable to receive textual and graphical information and processes the information for output to the display device.

Peripheral device(s) 1080 may include any type of computer support device to add additional functionality to the computer system.

The components provided in the computer system 1000 in FIG. 10 are those typically found in computer systems that may be suitable for use with embodiments of the present disclosure and are intended to represent a broad category of such computer components that are well known in the art. Thus, the computer system 1000 in FIG. 10 can be a personal computer (PC), hand held computer system, telephone, mobile computer system, workstation, tablet, phablet, mobile phone, server, minicomputer, mainframe computer, wearable, or any other computer system. The computer may also include different bus configurations, networked platforms, multi-processor platforms, and the like. Various operating systems may be used including UNIX, LINUX, WINDOWS, MAC OS, PALM OS, QNX, ANDROID, IOS, CHROME, and other suitable operating systems.

Some of the above-described functions may be composed of instructions that are stored on storage media (e.g., computer-readable medium). The instructions may be retrieved and executed by the processor. Some examples of storage media are memory devices, tapes, disks, and the like. The instructions are operational when executed by the processor to direct the processor to operate in accord with the technology. Those skilled in the art are familiar with instructions, processor(s), and storage media.

In some embodiments, the computing system 1000 may be implemented as a cloud-based computing environment, such as a virtual machine and/or container operating within a computing cloud. In other embodiments, the computing system 1000 may itself include a cloud-based computing environment, where the functionalities of the computing system 1000 are executed in a distributed fashion. Thus, the computing system 1000, when configured as a computing cloud, may include pluralities of computing devices in various forms, as will be described in greater detail below.

In general, a cloud-based computing environment is a resource that typically combines the computational power of a large grouping of processors (such as within web servers)

and/or that combines the storage capacity of a large grouping of computer memories or storage devices. Systems that provide cloud-based resources may be utilized exclusively by their owners or such systems may be accessible to outside users who deploy applications within the computing infrastructure to obtain the benefit of large computational or storage resources.

The cloud is formed, for example, by a network of web servers that comprise a plurality of computing devices, such as the computing system 1000, with each server (or at least a plurality thereof) providing processor and/or storage resources. These servers manage workloads provided by multiple users (e.g., cloud resource customers or other users). Typically, each user places workload demands upon the cloud that vary in real-time, sometimes dramatically. The nature and extent of these variations typically depends on the type of business associated with the user.

It is noteworthy that any hardware platform suitable for performing the processing described herein is suitable for use with the technology. The terms "computer-readable storage medium" and "computer-readable storage media" as used herein refer to any medium or media that participate in providing instructions to a CPU for execution. Such media can take many forms, including, but not limited to, non-volatile media, volatile media and transmission media. Non-volatile media include, for example, optical, magnetic, and solid-state disks, such as a fixed disk. Volatile media include dynamic memory, such as system random-access memory (RAM). Transmission media include coaxial cables, copper wire and fiber optics, among others, including the wires that comprise one embodiment of a bus. Transmission media can also take the form of acoustic or light waves, such as those generated during radio frequency (RF) and infrared (IR) data communications. Common forms of computer-readable media include, for example, a floppy disk, a flexible disk, a hard disk, magnetic tape, any other magnetic medium, a CD-ROM disk, digital video disk (DVD), any other optical medium, any other physical medium with patterns of marks or holes, a RAM, a programmable read-only memory (PROM), an erasable programmable read-only memory (EPROM), an electrically erasable programmable read-only memory (EEPROM), a Flash memory, any other memory chip or data exchange adapter, a carrier wave, or any other medium from which a computer can read.

Various forms of computer-readable media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU.

Computer program code for carrying out operations for aspects of the present technology may be written in any combination of one or more programming languages, including an object oriented programming language such as JAVA, SMALLTALK, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of wired and/or wireless network, including a (wireless) local area network (LAN/WLAN) or a (wireless) wide area network (WAN/WWAN), or the connection may be made to an external computer (for example, through the Internet using an Internet Service Provider, wireless Internet provider, and the like).

Figure 11A:
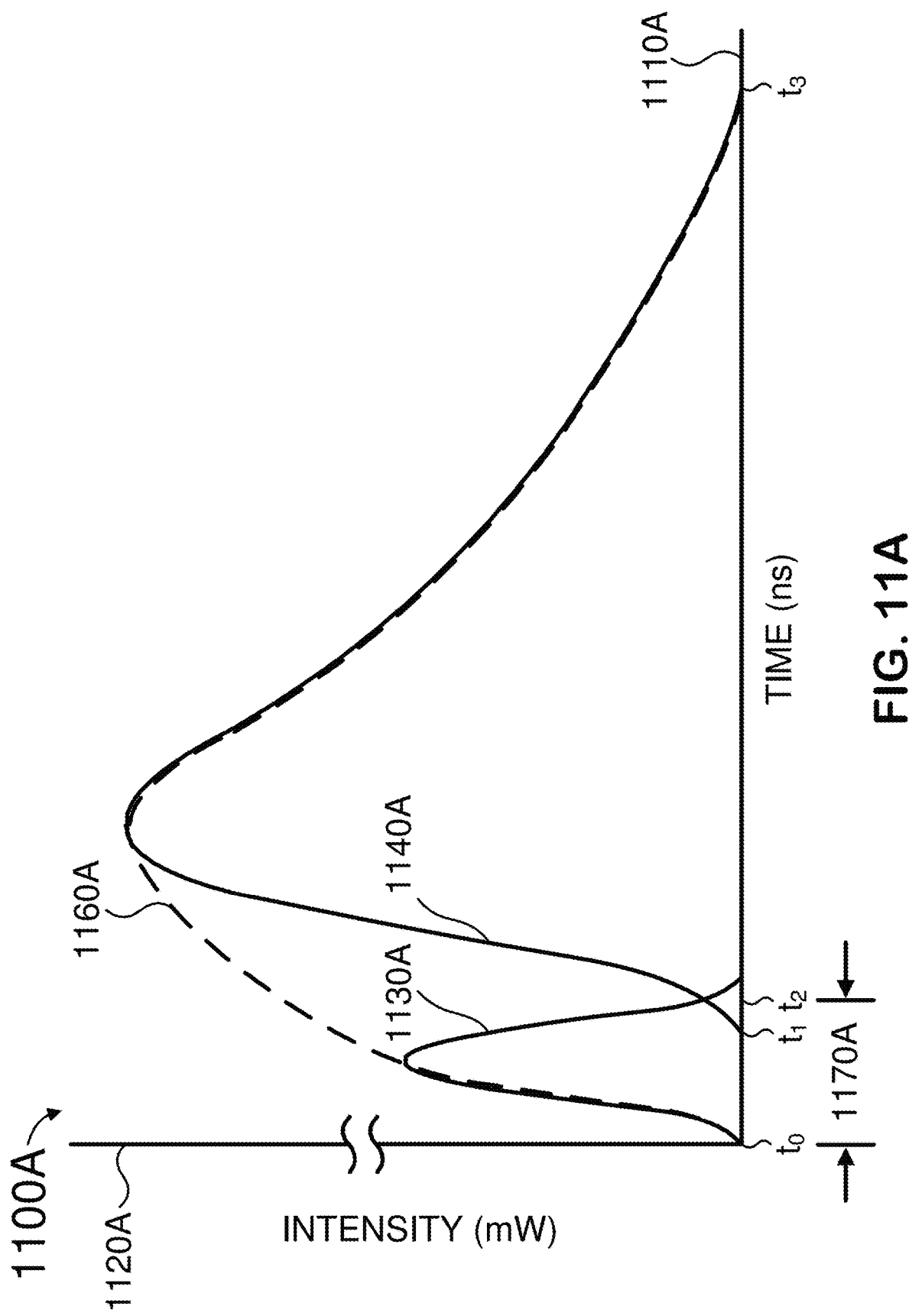
FIG. 11A is a simplified graphical representation of timing, in accordance with some embodiments.

FIG. 11A shows graphical representation (e.g., plot, graph, and the like) 1100A of (relative) (received) light intensity (e.g., in milliwatts (mW)) along axis 1120A over time (e.g., in nanoseconds) along axis 1110A. Graphical representation 1100A includes Raman signal 1130A, fluorescence 1140A, and total signal 1160A, according to some embodiments. Raman signal 1130A is, by way of non-limiting example, a Raman spectrograph for a material to be measured (e.g., analyte 150A-C in FIGS. 1-3). Total signal 1160A can be an intensity measured by a detector (e.g., detector 130 in FIG. 1) from (approximately) time $t_0$ to time $t_3$. As described above in relation to FIG. 5, fluorescence 1140A can be several orders of magnitude (e.g., $10^5$-$10^6$) higher in intensity than Raman signal 1130A and can overwhelm or obscure Raman signal 1130A, such that Raman signal 1130A is difficult to measure.

When light (e.g., light 160A in FIG. 1) from an excitation source (e.g., excitation light source 120 in FIG. 1) illuminates a material to be measured (e.g., analyte 150A in FIG. 1, 150B in FIG. 2, 150C in FIG. 3), receipt of the Raman signal (also called Raman scatter or return signal) 1130A by a detector (e.g., detector 136 in FIG. 1) is almost instantaneous (e.g., ≤1 ps, depending on the distance traveled by the light and the Raman signal) (e.g., at time $t_0$). For this reason, Raman signal 1130A can also be thought of as (approximately) representing the light from the excitation source, such as a laser pulse. In contrast, fluorescence 1140A is received/occurs after Raman signal 1130A (e.g., at time $t_1$). When light from the excitation source illuminates the material to be measured (e.g., at time $t_0$), receipt of fluorescence 1140A by the detector occurs later (e.g., at time $t_1$, which can be hundreds of nanoseconds or even milliseconds later).

When the detector (e.g., detector 136 in FIG. 1) is active (e.g., measuring light) while Raman signal 1130A is present and before fluorescence 1140A obscures/interferes with Raman signal 1130A (e.g., from time $t_0$ to time $t_2$), Raman signal 1130A can be measured by the detector without being overwhelmed or obscured by fluorescence 1140A. Time window 1170A is (ideally) the time during which Raman signal 1130A is present and fluorescence 1140A (mostly) is not present (e.g., from time $t_0$ to time $t_2$). As shown in FIG. 11A, although fluorescence 1140A begins being received at time $t_1$, an intensity of fluorescence 1140A may not be high enough to overwhelm or obscure fluorescence 1140A until at or after time $t_2$. Control of the detector such that the detector is substantially active only during time window 1170A can be referred to as gating. Moreover, time window 1170A can also be referred to as gate 1170A. Gating can be used to reject a significant portion of fluorescence 1140A.

In some embodiments, the detector (e.g., detector 136 in FIG. 1) is active (e.g., gate 1170A in FIG. 11A begins) prior to the excitation source (e.g., excitation light source 120 in FIG. 1) providing light. By way of non-limiting example, (ideal) gate 1170A is 1 ns (1,000 ps). The time resolution of the detector using the 1 ns (ideal) gate 1170A is approximately equal to the laser pulse duration (e.g., 600 ps).

Figure 11B:
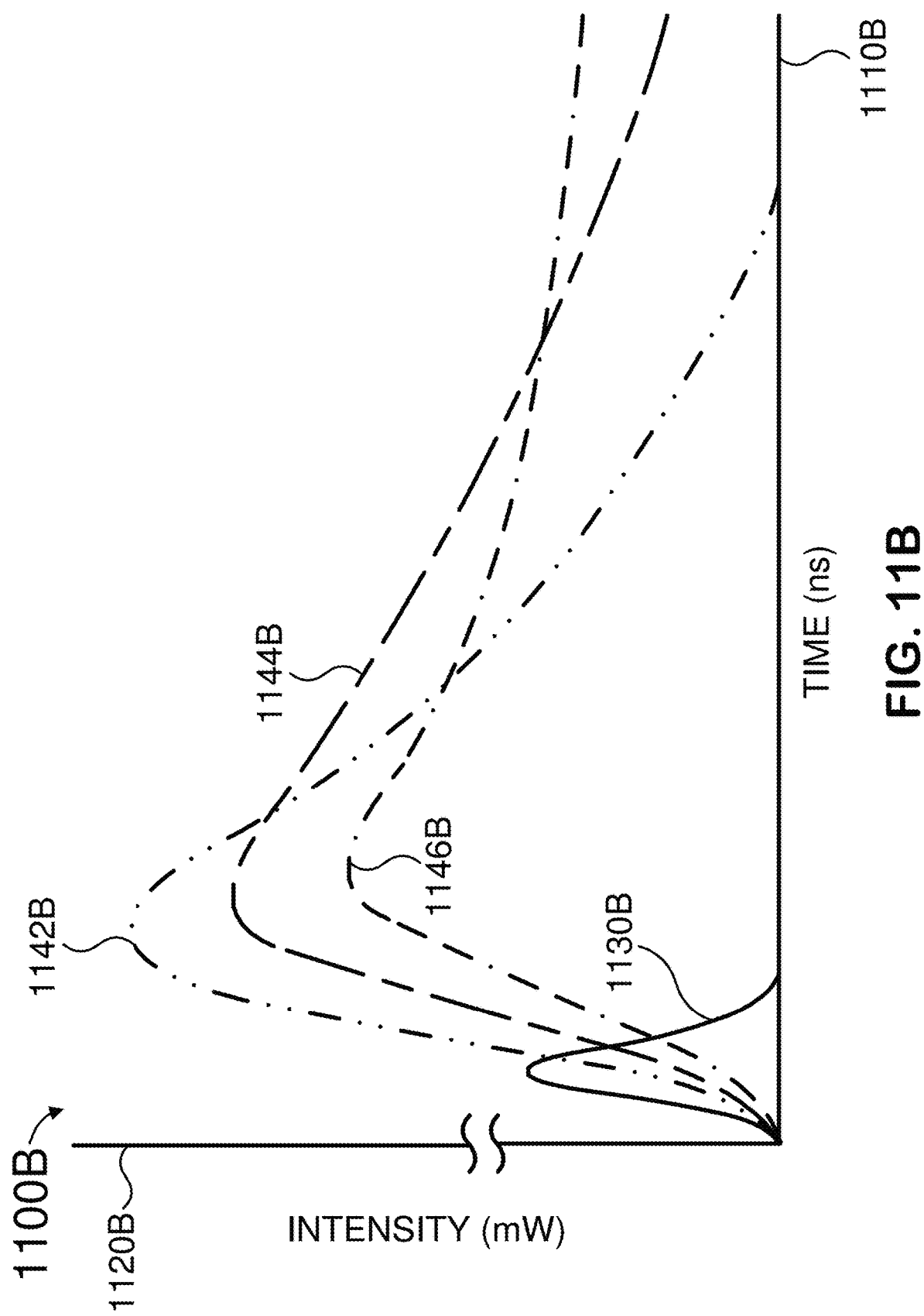
FIG. 11B is a simplified graphical representation of duration and intensity, in accordance with various embodiments.

FIG. 11B depicts graphical representation (e.g., plot, graph, and the like) 1100B of (relative) (received) light intensity (e.g., in milliwatts (mW)) (along axis 1120B) over time (e.g., in nanoseconds) along axis 1110E from a (e.g., 600 ps) laser pulse, in accordance with some embodiments. Graphical representation 1100B can include Raman signal 1130B and fluorescence 1142B-1146B. Graphical representation 1100B can show relative intensities and/or lifetimes/ durations of Raman signal 1130B and fluorescence 1142B-1146B. Raman signal 1130B has at least some of the characteristics of Raman signal 1130A described above in relation to FIG. 11A. Since Raman scattering occurs almost immediately (e.g., 1 ps, depending on the distance travelled by the light and the Raman signal) after an excitation light pulse from the excitation source (e.g., excitation light source 120 in FIG. 1), Raman signal 1130B can also (approximately) represent the excitation light pulse.

Graphical representation 1100B illustrates the relative intensities and/or the relative lifetimes/durations among fluorescence 1142B-1146B, according to various embodiments. Fluorescence 1142B-1146B can have at least some of the characteristics of fluorescence 1140A, as described above in relation to FIG. 11A. As shown in FIG. 11B, each of fluorescence 1142B-1146B can have a different lifetime/duration, with fluorescence 1142B having the shortest and fluorescence 1146B having the longest. By way of non-limiting example, fluorescence 1142B has a 1 ns lifetime/duration, fluorescence 1144B has a 5 ns lifetime/duration, and fluorescence 1144B has a 10 ns lifetime/duration. Depending upon the material, a fluorescence can have other lifetimes/durations (e.g., 100 ps-10 ms). Fluorescence 1142B-1146B can each be from a different material, resulting in different lifetimes/durations and intensities. As shown in FIG. 11B, the longer the lifetime/duration of a respective one of fluorescence 1142B-1146B, the lower the intensity of a respective one of fluorescence 1142B-1146B can be.

Figure 12:
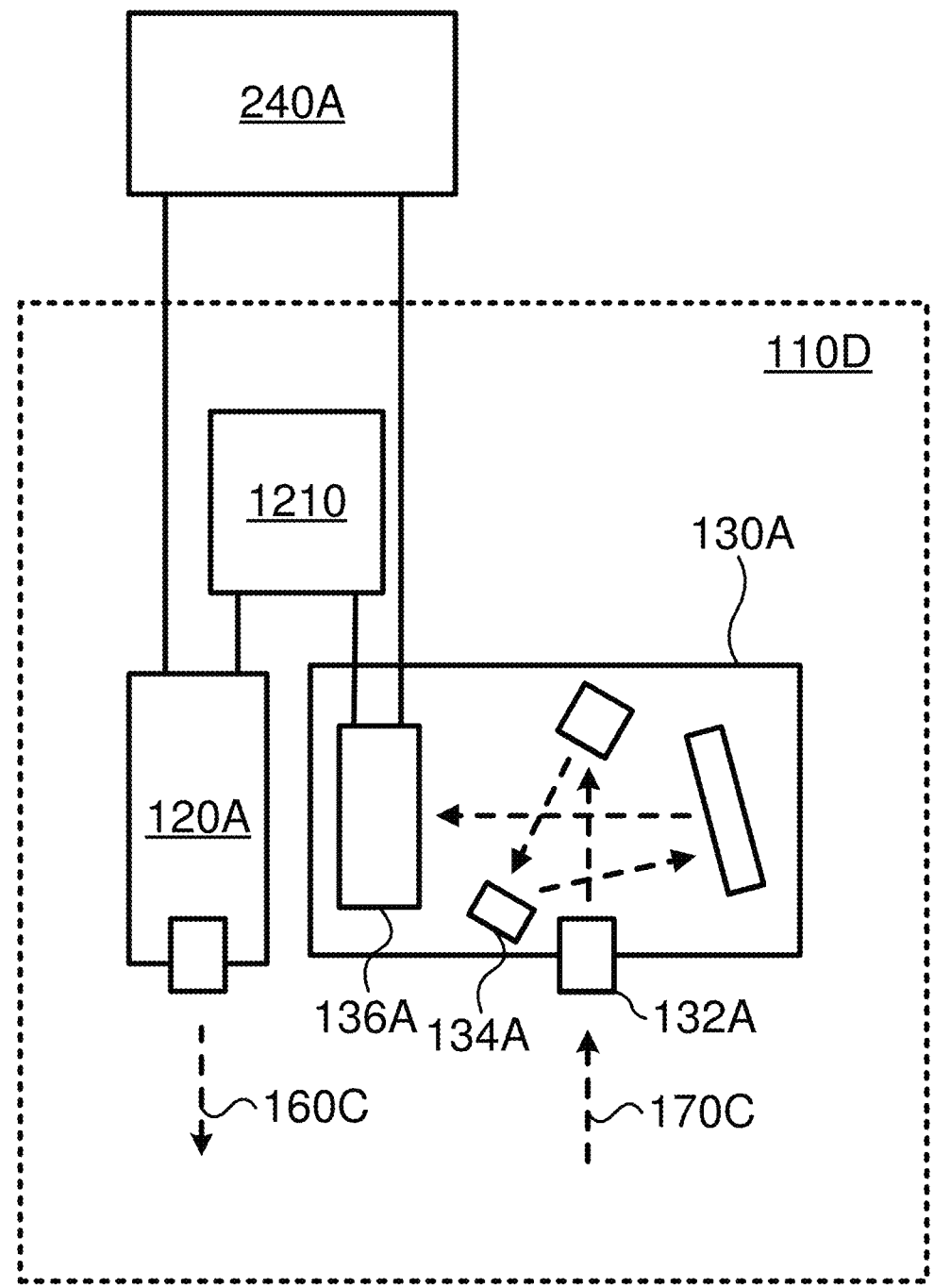
FIG. 12 is a simplified representation of a system for time-resolved spectroscopy, according to some embodiments.

FIG. 12 illustrates system 1200 for time-resolved spectroscopy in accordance with some embodiments. System 1200 includes Raman instrument 110D and computing system 240A. Raman instrument 110D has at least some of the characteristics of Raman instrument 110A (FIG. 1), Raman instrument 110E (FIG. 2), and Raman instrument 110C (FIG. 3). For example, Raman instrument 110D includes excitation light source 120A and detector 130A, as described above in relation to excitation light source 120 and detector 130 (respectively) in FIG. 1. By way of further non-limiting example, detector 130A includes slit 132A, spectral dispersion element 134A, and detector 136A, as described above in relation to slit 132, spectral dispersion element 134, and detector 136 (respectively) in FIG. 1. Computing system 240A has at least some of the characteristics of computing system 240 (FIG. 2) and computing system 1000 (FIG. 10). Although not depicted for pictorial clarity, system 1200 can additionally and/or alternatively include further elements described above in relation to system 100 (FIG. 1), system 200 (FIG. 2), and system 300 (FIG. 3).

Raman instrument 110D can further include delay 1210 for gating, according to some embodiments. Delay 1210 can be communicatively coupled to excitation light source 120A and detector 136A. In various embodiments, delay 1210 can detect when excitation light source 120A provides light 160C (e.g., a laser pulse is emitted). For example, delay 1210 can have a sensor (not depicted in FIG. 12) which detects light 160C being emitted from excitation light source 120A. By way of further non-limiting example, excitation light source 120A can provide a (electronic) signal to delay 1210 when excitation light source 120A provides light 160C (e.g., fires laser pulse). A predetermined amount of time after light 160C is detected/signaled, delay 1210 can provide a signal indicating to detector 136A to (effectively) stop detecting and provide measurements. The predetermined amount of time can be a gate (e.g., time window 1170A in FIG. 11A). For example, the predetermined amount of time (e.g., gate or time window) can be selected using the duration of light 160C (e.g., a laser pulse), characteristics of the material being measured (e.g., duration/lifetime of fluorescence), and the like.

Delay 1210 can be an (programmable) analog (e.g., continuous time) and/or digital (e.g., discrete time) delay line. In some embodiments, delay 1210 is a network of electrical components connected in series, where each individual element creates a time difference between its input signal and its output signal. In various embodiments, delay 1210 comprises one or more delay elements (e.g., forming a (circular) buffer) such as in discrete logic (e.g., flip flops, inverters, digital (or voltage) buffer, and the like), (general purpose) microprocessor, digital signal processor, application specific standard product (ASSP), application-specific integrated circuit (ASIC), field-programmable gate array (FPGA), and the like. Although depicted as a part of Raman instrument 110D, delay 1210 can alternatively be external to Raman instrument, such as part of computing system 240A.

According to some embodiments, detector 136A detects returned light 170C (e.g., Raman signal or scatter) during time window (or gate) 1170A (FIG. 11A) or in less time. Time window 1170A is the time during which Raman signal 1130A is present and before fluorescence 1140A obscures Raman signal 1130A (e.g., from time t0 to time t2), as shown in FIG. 11A. Depending upon the material to be measured (e.g., analyte 150A in FIG. 1, 150B in FIG. 2, 150C in FIG. 3) and the characteristics of light 160C (e.g., duration and wavelength of the laser pulse), time window 1170A can be in a range of hundreds of picoseconds to nanoseconds (e.g., 500 picoseconds to 2 nanoseconds). For example, time window 1170A can be 1 nanosecond. Accordingly, detector 136A can have a time resolution of (e.g., detect returned light 170C in) approximately one nanosecond or less.

By way of non-limiting example, detector 136A is a single-photon avalanche diode (SPAD) array. A SPAD is a solid-state photodetector in which a photon-generated carrier (via the internal photoelectric effect) can trigger a short-duration but relatively large avalanche current. The leading edge of the avalanche pulse marks the arrival (time) of the detected photon. The avalanche current can continue until the avalanche is quenched (e.g., by lowering a bias voltage down to a breakdown voltage). According to various embodiments, each pixel in some SPAD arrays can count a single photon and the SPAD array can provide a digital output (e.g., a 1 or 0 to denote the presence or absence of a photon for each pixel).

To detect another photon, a control circuit(s) (not depicted in FIG. 12) integrated in and/or external to the SPAD can be used to read out measurements and quench the SPAD. For example, the control circuit can sense the leading edge of the avalanche current, generate a (standard) output pulse synchronous with the avalanche build up, quench the avalanche, and restore the diode to an operative level. The control circuit can provide passive quenching (e.g., passive quenching passive reset (PQPR), passive quench active reset (PQAR), and the like) and/or active quenching (e.g., active quench active reset (AQAR), active quenching passive reset (AQPR), and the like). In various embodiments, detector 136A is a complementary metal-oxide semiconductor (CMOS) SPAD array.

Detector 136A can be other photodetectors having a time resolution of about one nanosecond or less. By way of further non-limiting example, detector 136A is a streak camera array, which can have a time-resolution of around 180 femtoseconds. A streak camera measures the variation in a pulse of light's intensity with time. A streak camera can transform the time variations of a light pulse into a spatial profile on a detector, by causing a time-varying deflection of the light across the width of the detector.

A spectral resolution of a spectrum measured by detector 136A can depend on the number of pixels (e.g., discrete photodetectors) in detector 136A. A greater number of pixels can provide a higher spectral resolution. Detector 136A can comprise a one-dimensional and/or two-dimensional array of pixels. For example, detector 136 has in a range of 32 to 1,048,576 pixels. According to some embodiments, detector 136 has in a range of 512 to 1,024 pixels.

In some embodiments, the output (e.g., measurements) from detector 136A is provided to an analog-to-digital converter (ADC) (not shown in FIG. 12). The ADC can be integrated into detector 136A or separate from detector 136A, such as in at least one of detector 130A, Raman instrument 110D, and computing system 240A. The ADC can convert the measurements before the next measurements are received. For example, when measurements are received at 20 KHz, the ADC can convert at 20 KHz or faster. When the output of detector 136A is already a digital spectra, analog-to-digital conversion is not needed.

Computing system 240A can be various combinations and permutations of stand-alone computers (e.g., smart phone, phablet, tablet computer, notebook computer, desktop computer, etc.) and resources in a cloud-based computing environment. Although depicted as outside of Raman instrument 110D, additionally or alternatively at least part of computing system 240A can be integrated into Raman instrument 110D.

Figure 13:
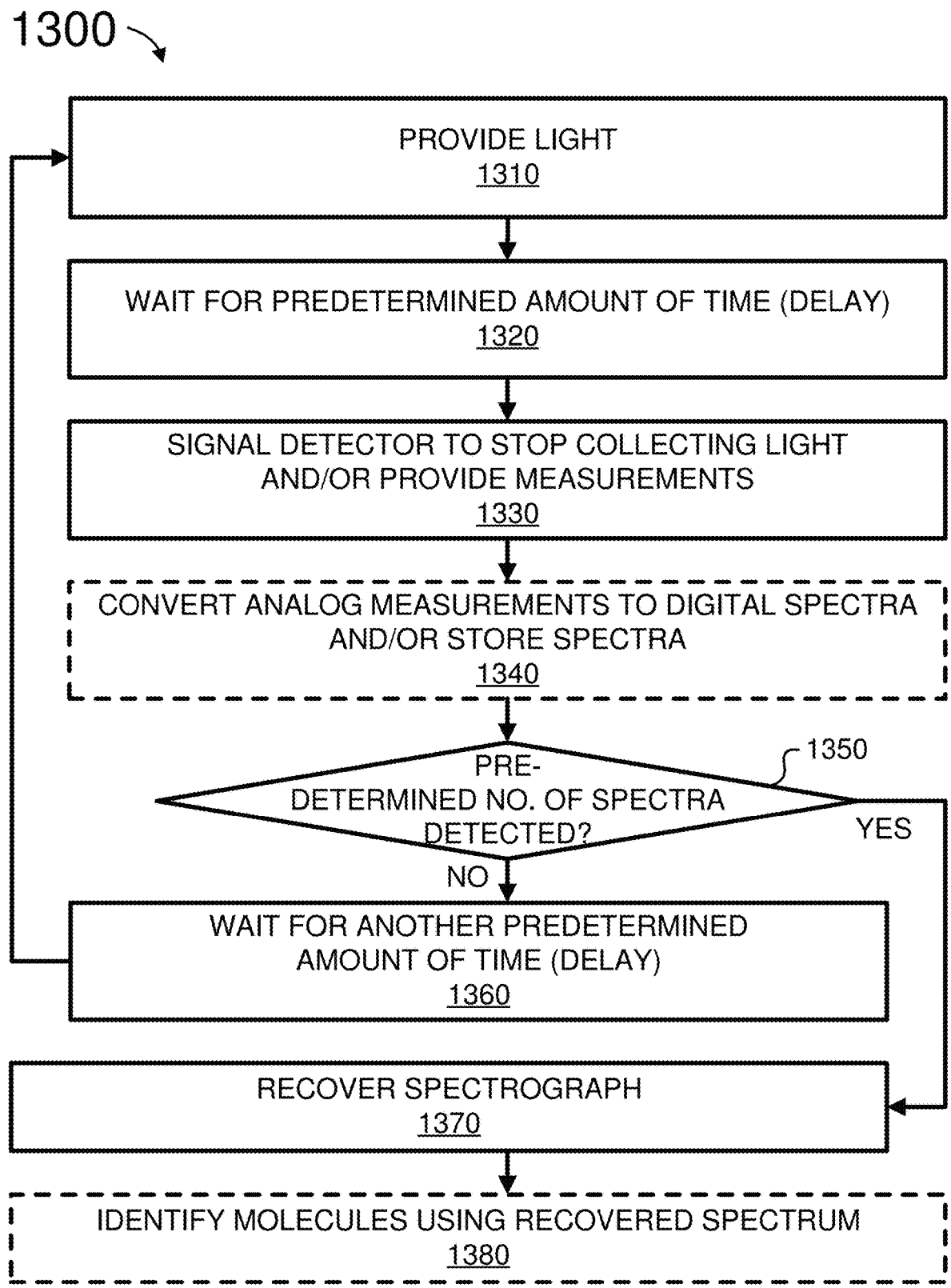
FIG. 13 is a simplified flow diagram of a method for time resolved spectroscopy, according to various embodiments.

FIG. 13 illustrates method 1300 for time resolved spectroscopy, according to some embodiments. Method 1300 can be performed by all or part of system 1200 (FIG. 12). Method 1300 can commence at step 1310, where light can be provided. The provided light can illuminate a material to be measured (e.g., analyte 150A-C in FIGS. 1-3). For example, the light can be provided by excitation light source 120A (FIG. 12) and directed to the material to be measured. By way of further non-limiting example, the provided light is a laser pulse.

In some embodiments, the provided light has a predetermined wavelength and/or duration. For example, the predetermined wavelength (also called an excitation wavelength) can depend on the material to be measured and be selected to minimize absorption (by the material) of the provided light and maximize the Raman signal, such as described above in relation to FIGS. 4A-4B. In addition, a shorter excitation wavelength can provide a stronger Raman signal than a longer excitation wavelength. In some embodiments, the excitation wavelength is in a range of 450 nm-650 nm.

By way of further non-limiting example, the predetermined duration can be selected so as to at least provide a Raman signal of sufficient duration to be measured by detector 136A, such as the gate (e.g., time window 1170A in FIG. 11A). At or after the receipt or occurrence of fluorescence, the provided light is not needed and may stop. In various embodiments, the predetermined duration is in a range of 200 ps-2 ns. For example, the predetermined duration is on the order of 600 ps.

At step 1320, method 1300 can wait or pause for a predetermined delay. In some embodiments, the predetermined delay can be controlled by delay 1210 in FIG. 12. For example, the predetermined delay can be substantially the duration of the gate (e.g., time window 1170A in FIG. 11A), which can depend on the material to be measured. Additionally or alternatively, the predetermined delay can also take into account latency (delays) arising from detection of the light being provided (e.g., laser firing), detector 136A de-activating after receipt of the instruction or control signal, characteristics of the material, and the like. For example, the preceding example latencies in system 1200 (FIG. 12) can be characterized and delay 1210 calibrated to take into them account (or otherwise compensate for them).

At step 1330, the detector (e.g., detector 136A in FIG. 12) can be signaled to stop collecting returned light and/or provide measurements. In some embodiments, an instruction or control signal can be provided to the detector (e.g., detector 136A and/or a control circuit(s) for detector 136A), which de-activates the detector (e.g., detector 136A stops measuring light/photons, outputs the light measurements, and/or optionally resets detector 136A to detect further photons such as by quenching). Although not shown in FIG. 13, method 1300 can receive the provided measurements.

At step 1340, the provided (received) measurements can be (optionally) converted to a digital spectra (e.g., using an ADC) and/or the digital spectra can be stored. In some embodiments, when detector 136A is a SPAD array which provides a digital output, the measurements (e.g., spectra) from detector 136A are already digital spectra and do not need a conversion, but can still be stored.

At step 1350, a determination is made as to whether another spectrum is to be detected. In some embodiments, the predetermined number of spectra to be detected (P) is compared to the number of spectra (actually) detected. When the predetermined number of spectra to be detected (P) is less than the number of spectra detected, method 1300 can proceed to step 1360. When the predetermined number of spectra to be detected (P) is equal to the number of spectra actually detected, method 1300 can proceed to step 1370.

Steps 1310-1340 can be repeated in a range of 9-9,999,999 times (e.g., P=10-1,000,000,000). For example, P can be in a range of 1,000-10,000 times. By way of further non-limiting example, P can be 1,000,000 samples taken in 50 seconds at a sample rate (e.g., steps 1310-1340 are repeated) of 20 kHz. In 50 seconds, some measurable characteristics of the material to be measured (e.g., analyte 150A-C in FIGS. 1-3) do not appreciably change (e.g., an accurate reading can be performed). In some embodiments, there is latency (a delay) between when detector 136A receives an instruction or control signal to de-activate and when detector 136A actually de-activates. This latency can be, for example, 10 ps-1,000 ps. In some embodiments, this latency is on the order of 100 ps. For example, when detector 136A continues measuring after the end of the gate (e.g., time window 1170A in FIG. 11A, at time $t_2$,), detector 136A will measure at least some fluorescence.

In addition, detector 136A may detect ambient/background radiation. Ambient/background radiation can include one or more of: Ultraviolet C (UVC) light (e.g., 100 nm-280 nm wavelength), Ultraviolet B (UVB) light (e.g., 280 nm-315 nm wavelength), Ultraviolet A (UVA) light (e.g., 315 nm-400 nm wavelength), visible light (e.g., 380 nm-780 nm wavelength), and infrared (e.g., 700 nm-1 mm wavelength). To reduce the distortion (to the measured spectra) introduced by fluorescence and/or ambient/background radiation, multiple measurements can be taken, since the measured fluorescence and/or ambient/background radiation can vary across multiple measurements.

At step 1360, method 1300 can wait or pause for another predetermined delay before proceeding back to step 1310. The another predetermined delay determines at least partially a frequency at which light is provided to (e.g., a laser fires at) the material and the returned light measured. The provided light (e.g., laser pulses) can be temporally spaced, such that at least the fluorescence from the material dies out (e.g., the end of the fluorescence lifetime is reached) before the next laser pulse is sent out. In other words, the time between laser pulses (e.g., the another predetermined delay) can be longer than the fluorescence lifetime/duration (e.g., FIG. 11B). Additionally or alternatively, the another predetermined delay can be selected such that when detector 136A is a SPAD array, each pixel in the SPAD array can be quenched (and ready to detect a photon) before light is provided again at step 1310.

In some embodiments, the frequency at which the light is provided (e.g., the laser fires) can be in the range of 1 KHz-100 KHz. For example, the frequency is on the order of tens of kilohertz, such as 20 KHz (e.g., the another predetermined delay (uncompensated) is 50 ms). The another predetermined delay can be adjusted to compensate for latency (delays) incurred by at least some of steps 1310-1350 (e.g., the time is takes to perform at least some of steps 1310-1350). The another predetermined delay can be different from the predetermined delay.

At step 1370, a (Raman) spectrum or spectrograph (e.g., intensity at one or more wavelengths) of the material can be recovered using the detected spectra (e.g., P detected spectra). In some embodiments, the (Raman) spectrum or spectrograph (e.g., intensity at one or more wavelengths) of the material can be recovered by summing the detected spectra. Since the measured fluorescence and noise introduced by ambient light can vary across multiple measurements, summing multiple measurements can reduce/eliminate distortions introduced by fluorescence and/or ambient light. Additionally or alternatively, statistical methods (e.g., arithmetic mean, rolling average, and the like) can be used to recover the (Raman) spectrum or spectrograph. The recovered (Raman) spectrum or spectrograph may appear (e.g., when graphed/plotted) as shown in graphical representation 500 (FIG. 5) (e.g., Raman signal 530 (530A-D) substantially without fluorescence 540).

Optionally at step 1380, a molecule (and optionally a concentration of the molecule) can be identified using the recovered (Raman) spectrum. In some embodiments, the recovered (Raman) spectrum or spectrograph (e.g., intensity at one or more wavelengths) can be calibrated using one or more optical phantoms. For example, steps 1310-1370 can be applied to an optical phantom which mimics the material to be tested. In the case of biological analytes, optical phantoms are tissue-simulating objects used to mimic light propagation in living tissue. Optical phantoms can be designed with absorption and scattering properties matching optical characteristics of living human and animal tissues.

By way of further non-limiting example, steps 1310-1370 can be applied (one or more times) to optical phantoms, each optical phantom having/mimicking a different concentration of a particular molecule (FIG. 9). During calibration, the resulting recovered spectrum from each phantom/concentration can be correlated with the molecule (and concentration) of that optical phantom. Using calibration, the correlation between the recovered (Raman) spectrum or spectrograph (e.g., intensity at one or more wavelengths) of the material to be measured and the presence/concentration of a certain molecule can be established. In some embodiments, the spectra generated during the calibration process are stored in a database and the actual spectrum produced when taking real measurements can be compared to the stored spectra. The characteristics of a matching stored spectrum can be associated with the actual spectrum.

Additionally, calibration using optical phantoms for other molecules at different concentrations can be performed. Although a calibration process for detecting a range of concentrations is described, calibration can be performed for detecting the presence of a molecule (e.g., using a phantom having a minimum, threshold, or maximum concentration of the molecule).

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the invention in the form disclosed. Many modifications and variations will be apparent to those of ordinary skill in the art without departing from the scope and spirit of the invention. Exemplary embodiments were chosen and described in order to best explain the principles of the present technology and its practical application, and to enable others of ordinary skill in the art to understand the invention for various embodiments with various modifications as are suited to the particular use contemplated.

Aspects of the present technology are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present technology. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The description of the present technology has been presented for purposes of illustration and description, but is not intended to be exhaustive or limited to the invention in the form disclosed. Many modifications and variations will be apparent to those of ordinary skill in the art without departing from the scope and spirit of the invention. Exemplary embodiments were chosen and described in order to best explain the principles of the present technology and its practical application, and to enable others of ordinary skill in the art to understand the invention for various embodiments with various modifications as are suited to the particular use contemplated.

What is claimed is:

1. A method for time-resolved spectroscopy comprising:
providing first light using an excitation source;
receiving first scattered light from a material responsive to the providing the first light using a detector;
signaling the detector, after a delay commencing after the providing the first light, to provide a first spectrum of the received first scattered light, the delay being a predetermined amount of time beginning when the excitation source emits light, the delay being selected based on characteristics of the material;
providing second light using the excitation source;
receiving second scattered light from the material responsive to the providing the second light using the detector;
signaling the detector, after a delay commencing after the providing the second light, to provide a second spectrum of the received second scattered light;
providing third light using the excitation source;
receiving third scattered light from the material responsive to the providing the third light using the detector;
signaling the detector, after a delay commencing after the providing the third light, to provide a third spectrum of the received third scattered light;
recovering a spectrum of the material using the first spectrum, the second spectrum, and the third spectrum; and
identifying at least one molecule of the material using the recovered spectrum and a database of identified spectra.

2. The method of claim 1, wherein the delay is an amount of time during which scattered light from the material responsive to the provided light is present and after which the scattered light from the material responsive to the provided light is obscured by fluorescence.

3. The method of claim 1, wherein the predetermined amount of time is in a range of 500 ps to 1,500 ps.

4. The method of claim 1, wherein the detector comprises an array of single-photon avalanche diodes.

5. The method of claim 1, wherein the first light, the second light, and the third light are provided sequentially at a predetermined frequency, such that a period of the predetermined frequency is greater than a lifetime of fluorescence from the material.

6. The method of claim 5, wherein the predetermined frequency is within a range from 1 KHz to 100 KHz.

7. The method of claim 1, wherein the providing the first light, the second light, and the third light has a predetermined duration within a range from 500 ps to 1,500 ps.

8. The method of claim 1, wherein the first light, the second light, and the third light have a predetermined wavelength within a range from 650 nm to 950 nm.

9. The method of claim 1, wherein the excitation source is a tunable laser.

10. The method of claim 1, wherein the material is at least one of living plant and animal tissue.

11. A system for time-resolved spectroscopy comprising:
a monochromatic light source, the monochromatic light source:
providing first light, second light, and third light;
a detector, the detector:
receiving first scattered light from a material responsive to the providing the first light;
receiving second scattered light from the material responsive to the providing the second light; and
receiving third scattered light from the material responsive to the providing the third light;
a circuit, the circuit:
signaling the detector, after a delay commencing after the providing the first light, to provide a first spectrum of the received first scattered light, the delay being a predetermined amount of time beginning when the monochromatic light source emits light, the delay being selected based on characteristics of the material;
signaling the detector, after a delay commencing after the providing the second light, to provide a second spectrum of the received second scattered light; and
signaling the detector, after a delay commencing after the providing the third light, to provide a third spectrum of the received third scattered light; and
a processor, the processor:
recovering a spectrum of the material using the first spectrum, the second spectrum, and the third spectrum; and
identifying at least one molecule of the material using the recovered spectrum and a database of identified spectra.

12. The system of claim 11, wherein the delay is an amount of time during which scattered light from the material responsive to the provided light is present and after which the scattered light from the material responsive to the provided light is obscured by fluorescence.

13. The system of claim 11, wherein the delay is in a range of 500 ps to 1,500 ps.

14. The system of claim 11, wherein the detector comprises an array of single-photon avalanche diodes.

15. The system of claim 11, wherein the first light, the second light, and the third light are provided sequentially at a predetermined frequency, such that a period of the predetermined frequency is greater than a lifetime of fluorescence from the material.

16. The system of claim 15, wherein the predetermined frequency is within a range from 1 KHz to 100 KHz.

17. The system of claim 11, wherein
the providing the first light, the second light, and the third light has a predetermined duration within a range from 500 ps to 1,500.

18. The system of claim 11, wherein the monochromatic light source is a tunable laser.

19. The system of claim 11, wherein the first light, the second light, and the third light have a predetermined wavelength within a range from 650 nm to 950 nm.

20. A system for time-resolved spectroscopy comprising:

means for providing first light using an excitation source, a second light using the excitation source, and a third light using the excitation source;

means for receiving first scattered light from a material responsive to the providing the first light using a detector;

means for signaling the detector, after a delay commencing after the providing the first light, to provide a first spectrum of the received first scattered light, the delay being a predetermined amount of time beginning when the excitation source emits light, the delay being selected based on characteristics of the material;

means for receiving second scattered light from the material responsive to the providing the second light using the detector;

means for signaling the detector, after a delay commencing after the providing the second light, to provide a second spectrum of the received second scattered light;

means for receiving third scattered light from the material responsive to the providing the third light using the detector;

means for signaling the detector, after a delay commencing after the providing the third light, to provide a third spectrum of the received third scattered light;

means for recovering a spectrum of the material using the first spectrum, second spectrum, and third spectrum; and means for identifying at least one molecule of the material using the recovered spectrum and a database of identified spectra.

* * * * *

UNITED STATES PATENT AND TRADEMARK OFFICE
CERTIFICATE OF CORRECTION

PATENT NO. : 10,876,892 B2
APPLICATION NO. : 15/847876
DATED : December 29, 2020
INVENTOR(S) : Yang et al.

It is certified that error appears in the above-identified patent and that said Letters Patent is hereby corrected as shown below:

On the Title Page

(72) should read:
William Yang   Los Altos Hills, CA
Leyun Zhu      Andover, MA
Chase Wang     Livermore, CA
Ming Chai      Union City, CA
Haolin Wang    San Jose, CA Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*